US007198791B2

(12) United States Patent
Pluschke et al.

(10) Patent No.: US 7,198,791 B2
(45) Date of Patent: Apr. 3, 2007

(54) COMPOSITIONS AND METHODS FOR THE GENERATION OF PROTECTIVE IMMUNE RESPONSES AGAINST MALARIA

(75) Inventors: Gerd Pluschke, Bad Kronzing (DE); Mueller Markus, Lorrach (DE); John Robinson, Wermatswil (CH); Rinaldo Zurbriggen, Schmitten (CH); Annabelle Freund-Renard, Schonenwerd (CH)

(73) Assignee: Pluschke, Gerd et al., Bad Kronzing (DE)

( * ) Notice: Subject to any disclaimer, the term of this patent is extended or adjusted under 35 U.S.C. 154(b) by 53 days.

(21) Appl. No.: 10/379,417

(22) Filed: Mar. 3, 2003

(65) Prior Publication Data

US 2004/0175392 A1    Sep. 9, 2004

(51) Int. Cl.
A61K 39/00 (2006.01)
A61K 39/38 (2006.01)
A61K 39/385 (2006.01)
A61K 38/00 (2006.01)
A01N 37/18 (2006.01)
C07K 16/00 (2006.01)
C07K 17/00 (2006.01)

(52) U.S. Cl. .............. 424/185.1; 424/184.1; 424/265.1; 424/268.1; 424/272.1; 424/193.1; 424/194.1; 514/2; 514/8; 514/12; 530/300; 530/324; 530/332

(58) Field of Classification Search ............ 424/185.1, 424/265.1, 268.1, 194.1, 184.1, 272.1, 193.1; 530/300, 350, 324, 332; 514/9, 2, 12, 8
See application file for complete search history.

(56) References Cited

U.S. PATENT DOCUMENTS

| 7,029,685 B2 * | 4/2006 | Lanar et al. | 424/272.1 |
| 7,060,276 B2 * | 6/2006 | Lanar et al. | 424/184.1 |
| 7,101,556 B2 * | 9/2006 | Pan | |
| 2003/0032787 A1 * | 2/2003 | Lanar et al. | 536/23.1 |
| 2004/0019971 A1 * | 2/2004 | Rhodes | 5/632 |
| 2004/0063190 A1 * | 4/2004 | Pan | 435/252.3 |
| 2004/0175392 A1 * | 9/2004 | Pluschke et al. | 424/185.1 |

FOREIGN PATENT DOCUMENTS

| WO | PCT/AU89/00056 | 8/1989 |
| WO | WO 89/07645 A1 * | 8/1989 |
| WO | PCT/US92/02207 | 10/1992 |
| WO | WO 92/16616 A1 * | 10/1992 |
| WO | WO 2002/16439 A2 * | 2/2002 |
| WO | WO 2002/77195 A2 * | 3/2002 |
| WO | WO 2002/52014 A2 * | 7/2002 |
| WO | WO 2002/72625 A1 * | 9/2002 |
| WO | PCT/EP2004/002126 | 9/2004 |

OTHER PUBLICATIONS

Mueller et al, Infection and Immunity, Aug. 2003, 71/8:4749-4758.*
Silvie et al, JBC, Mar. 5, 2004, 279/10:9490-9496.*
Pye et al, Infection and Immunity, Jul. 1991, 59/7:2403-2411.*
Crewther et al, Infection and Immunity, Aug. 1996, 64/8:3310-3317.*
Lal et al, Infection and Immuity, Mar. 1996, 64/3:1054-1059.*
Fu et al, HBC, Oct. 10, 1997, 272/41:25678-25684.*
Amante et al, J. Immunology, 1997, 159:5535-5544.*
Cubillos et al, Biochimie, 2003, 84:1181-1188.*
Mitchell et al, Infection and Immunity, Jan. 2004, 72/1:154-158.*
Anders et al, Parasitology Today, 2000, 16/10:444-447.*
Urquiza et al, Vaccine, 2001, 19:508-513.*
Arevalo-Herrera et al, Molecular Immunology, 2001, 38:443-455.*
Salvatore et al, Vaccine, 2002, 20:3477-3484.*
Polley et al, Vaccine, 2004, 23:718-728.*
Shi et al, Vaccine, 2000, 18:2902-2914.*
Kocken et al, Molecular and Biochemical Parasitology, 2000, 109:147-156.*
Donahue et al, Molecular and Biochemical Parasitology, 2000, 111:15-30.*
Figtree et al, Molecular and Biochemical Parasitology, 2000, 108:53-66.*
Feng et al, J. Mol. Biol., 2005, 350:641-656.*
Bruns et al, Vaccine, 2003, 21:1843-1852.*
Salazar et al, FEBS Letters, 2002, 527:95-100.*
Fraser et al, Molecular and Biochemical Parasitology, 2001, 117:49-59.*
Heppner et al, Vaccine, 2005, 23:2243-2250.*
Amit, A. G. et al., "Three-dimensional structure of an antigen-antibody complex at 2.8 A resolution," Science 233:747-753 (1986).
Anders, R. F. et al., "Immunisation with recombinant AMA-1 protects mice against infection with *Plasmodium chabaudi*," Vaccine 16:240-247 (1998).
Beeli, Reto et al., "A Tricyclic Template Derived from (2S,4R)-4-Hydroxyproline for the Synthesis of Protein Loop Mimetics," *Helvetica Chimica Acta* 79:2235-2248.
Bisang, Christian et al., "Protein-Loop Mimetics: A Diketopiperazine-Based Template to Stabilize Loop Conformation in Cyclic Peptides Containing the NPNA and RGD Motifs," *Helvetica Chimica Acta* 79:1825-1842 (1996).
Cheng, Qin et al., "Sequence Analysis of the Apical Membrane Antigen I (AMA-1) of *Plasmodium vivax*", Mol. Biochem. Parasitol. 65:183-187 (1994).

(Continued)

*Primary Examiner*—Nita Minnifield
(74) *Attorney, Agent, or Firm*—Proskauer Rose LLP

(57) ABSTRACT

The invention presents vaccine formulations comprising highly antigenic epitopes identified within the semi-conserved loop-I of domain III that are capable of eliciting parasite growth inhibitory antibodies. The cyclized or linear peptides can be applied by known adjuvants or be encapsulated by or attached onto the surface of liposomes or virosomes (IRIVs) which serve as human compatible antigen delivery systems. Both cyclized and linear versions of the peptide antigens are surprisingly effective in eliciting immune responses that are cross-reactive with parasite-expressed AMA-1.

24 Claims, 5 Drawing Sheets

OTHER PUBLICATIONS

Christodoulides, Myron et al., "Immunization with Recombinant Class 1 Outer-Membrane Protein from *Neisseria Meningitidus*: Influence of Liposomes and Adjuvants on Antibody Avidity, Recognition of Native Protein and the Induction of a Bactericidal Immune Response Against Meningococci," *Microbiology*, 144:3027-3037 (1998).

Cohen, S. et al., "Gamma globulin and acquired immunity to human malaria," *Nature* 192:733-737 (1961).

Coley, Andrew M. et al., "Rapid and precise epitope mapping of monoclonal antibodies against *Plasmodium falciparum* AMA1 by combined phage display of fragments and random peptides," *Protein Eng* 14:691-698 (2001).

Collins, W. E. et al., "Protective immunity induced in squirrel monkeys with recombinant apical membrane antigen-1 of *Plasmodium fragile*," *Am. J. Trop. Med. Hyg.* 51:711-719 (1994).

Crewther, P. E. et al., "*Plasmodium falciparum*: two antigens of similar size are located in different compartments of the rhoptry," *Exp. Parasitol.* 70:193-206 (1990).

Crewther, P. E. et al., "Protective immune responses to apical membrane antigen 1 of *Plasmodium chabaudi* involve recognition of strain-specific epitopes," *Infect. Immun.* 64:3310-3317 (1996).

Deans, J. A. et al., "Vaccination trials in rhesus monkeys with a minor, invariant, *Plasmodium knowlesi* 66kD merozoite antigen," *Parasite Immunol.* 10:535-552 (1988).

Deans, Judith A. et al., "Rat monoclonal antibodies which inhibit the in vitro multiplication of *Plasmodium knowlesi*," *Clin. Exp. Immunol.* 49:297-309 (1982).

Dorn, Arnulf et al., "Malarial haemozoin/beta-haematin supports haem polymerization in the absence of protein," *Nature* 374:269-271 (1995).

Escalante, Ananias A. et al., Polymorphism in the gene encoding the apical membrane antigen-1 (AMA-1) of *Plasmodium falciparum*. X. Asembo Bay Cohort Project. Mol. Biochem. Parasitol. 113:279-287 (2001).

Favre, Michel et al., "Structural Mimicry of Canonical Conformations in Antibody Hypervariable Loops Using Cyclic Peptides Containing a Heterochiral Diproline Template," *J. Am. Chem. Soc.* 121:2679-2685 (1999).

Fries, Louis F. et al., "Liposomal Malaria Vaccine in Humans: A Safe and Potent Adjuvant Strategy," *Proc. Natl. Acad. Sci. USA*, 89:358-362 (Jan. 1992).

Gluck, Reinhard, "Adjuvant activity of immunopotentiating reconstituted influenza virosomes (IRIVs)," *Vaccine* 17:1782-1787 (1999).

Gomme, Peter. T. et al., "Evaluation of a pepscan approach to identify epitopes recognised by anti-hTSH monoclonal antibodies," *J. Biochem. Biophys. Methods* 38:53-70 (1999).

Hodder, Anthony N. et al., "Specificity of the protective antibody response to apical membrane antigen 1," *Infect. Immun.* 69:3286-3294 (May 2001).

Hodder, Anthony N. et al., "The disulfide bond structure of Plasmodium apical membrane antigen-1," *J. Biol. Chem.* 271:29446-29452 (1996).

Howell, Steven A. et al., "Proteolytic processing and primary structure of *Plasmodium falciparum* apical membrane antigen-1," *J. Biol. Chem.* 276:31311-31320 (2001).

Kocken, Clemens H.M. et al., "Precise timing of expression of a *Plasmodium falciparum*-derived transgene in *Plasmodium berghei* is a critical determinant of subsequent subcellular localization," *J. Biol. Chem.* 273:15119-15124 (1998).

Kocken, Clemens H.M. et al., "High-level expression of the malaria blood-stage vaccine candidate *Plasmodium falciparum* apical membrane antigen 1 and induction of antibodies that inhibit erythrocyte invasion," *Infect. Immun.* 70:4471-4476 (2002).

Kocken, Clemens, H.M. et al., "Molecular characterisation of *Plasmodium reichenowi* apical membrane antigen-1 (AMA-1), comparison with *P. falciparum* AMA-1, and antibody-mediated inhibition of red cell invasion," *Mol. Biochem. Parasitol.* 109:147-156 (2000).

Kumar, Sanjai et al., "Vaccines against asexual stage malaria parasites," *Chem. Immunol.* 80:262-286 (2002).

Lambros, Chris and Vanderberg, J. P., "Synchronization of *Plasmodium falciparum* erythrocytic stages in culture," *J. Parasitol.* 65:418-420 (1979).

Marshall, Vikki M. et al., "Diversity of the vaccine candidate AMA-1 of *Plasmodium falciparum*," *Mol. Biochem. Parasitol.* 77:109-113 (1996).

Marshall, Vikki M. et al., "Structure of the apical membrane antigen I (AMA-1) of *Plasmodium chabaudi*," *Mol. Biochem. Parasitol.* 37:281-283 (1989).

Miller, Louis H. and Hoffman, Stephen L., "Research toward vaccines against malaria," *Nat. Med. Vaccine Supp.* 4:520-524 (May 1998).

Moreno, Rafael et al., "Exploiting conformationally constrained peptidomimetics and an efficient human-compatible delivery system in synthetic vaccine design," *Chembiochem* 2:838-843 (2001).

Nair, Margie et al., "Structure of Domain III of the Blood-stage Malaria Vaccine Candidate, *Plasmodium falciparum* Apical Membrane Antigen 1 (AMA1)," *J. Mol. Biol.* 322:741-753 (2002).

Narum, David L. and Thomas Alan W., "Differential localization of full-length and processed forms of PF83/AMA-1 an apical membrane antigen of *Plasmodium falciparum* merozoites," *Mol. Biochem. Parasitol.* 67:59-68 (1994).

Narum, David L. et al., Immunization with parasite-derived apical membrane antigen 1 or passive immunization with a specific monoclonal antibody protects BALB/c mice against lethal *Plasmodium yoelii yoelii* YM blood-stage infection, *Infect. Immun.* 68:2899-2906 (2000).

Peterson, M. Gregory et al., "Integral membrane protein located in the apical complex of *Plasmodium falciparum*," *Mol. Cell Biol.* 9:3151-3154 (1989).

Pfeifer, Marc E. et al., "Stabilisation of β-hairpin Conformations in a Protein Surface Mimetic Using a Bicyclic Template Derived from (2S,3R,4R)-Diaminoproline," *Chem. Commun.* 1977-78 (1998).

Polley, Spencer D. and Conway, David J., "Strong diversifying selection on domains of the *Plasmodium falciparum* apical membrane antigen 1 gene," *Genetics* 158:1505-1512 (2001).

Poltl-Frank, F. et al., "Use of reconstituted influenza virus virosomes as an immunopotentiating delivery system for a peptide-based vaccine," *Clin. Exp. Immunol.* 117:496-503 (1999).

Richie, Thomas L. and Saul, Allan, "Progress and challenges for malaria vaccines," *Nature* 415:694-701 (2002).

Sabchareon, A. et al., "Parasitologic and clinical human response to immunoglobulin administration in falciparum malaria," *Am. J. Trop. Med. Hyg.* 45:297-308 (1991).

Salvatore, Daniela et al., "Identification of antigenically active tryptic fragments of apical membrane antigen-1 (AMA1) of *Plasmodium chabaudi* malaria: strategies for assembly of immunologically active peptides," *Vaccine* 20:3477-3484 (2002).

Sheriff, Steven et al., "Three-dimensional structure of an antibody-antigen complex," *Proc. Natl. Acad. Sci. USA* 84:8075-8079 (1987).

Skehel, John J. et al., "The polypeptide composition of influenza A viruses," *Virology* 44:396-408 (1971).

Triglia, Tony et al., "Apical membrane antigen 1 plays a central role in erythrocyte invasion by Plasmodium species," *Mol. Microbiol.* 38:706-718 (2000).

Urquiza, Mauricio et al., "*Plasmodium falciparum* AMA-1 erythrocyte binding peptides implicate AMA-1 as erythrocyte binding protein," *Vaccine* 19:508-513 (2000).

Uthaipibull, Chairat et al., "Inhibitory and blocking monoclonal antibody epitopes on merozoite surface protein 1 of the malaria parasite *Plasmodium falciparum*," *J. Mol. Biol.* 307:1381-1394 (2001).

Verra, Federica and Hughes, Austin L, et al., "Evidence for ancient balanced polymorphism at the Apical Membrane Antigen-1 (AMA-1) locus of *Plasmodium falciparum*," *Mol. Biochem. Parasitol.* 105:149-153 (2000).

Waters, Andrew P. et al., "A merozoite receptor protein from Plasmodium knowlesi is highly conserved and distributed throughout Plasmodium," *J. Biol: Chem.* 265:17974-17979 (1990).

Xu, Huji et al., "CD4+ T cells acting independently of antibody contribute to protective immunity to *Plasmodium chabaudi* infection after apical membrane antigen 1 immunization," *J. Immunol.* 165:389-396 (2000).

Zhang, L. et al., "Sequence analysis of apical membrane antigen I from a *Plasmodium falciparum* isolate collected from Mengpeng Township, Yunnan Province," Zhongguo Ji. Sheng Chong. Xue. Yu Ji. Sheng Chong. Bing. Za Zhi 13:203-208 (1995). (Abstract).

* cited by examiner

Dilution of Anti-AMA49LISH Mouse Sera

COMPOSITIONS AND METHODS FOR THE GENERATION OF PROTECTIVE IMMUNE RESPONSES AGAINST MALARIA

FIELD OF THE INVENTION

The present invention relates to the fields of immunology, chemistry and molecular biology. Specifically, the invention relates to immunostimulatory compositions comprising epitopes from a malarial blood-stage protein that are capable of eliciting growth inhibitory immune responses.

BACKGROUND OF THE INVENTION

Various publications or patents are referred to in parentheses throughout this application to describe the state of the art to which this invention pertains. Each of these publications or patents is incorporated by reference herein.

With currently up to 300 million affected people, of whom between 2 and 3 million die each year, and an additional 2 billion people at risk of infection, malaria continues to be one of the major burden of public health in many tropical countries (44). Because of the spreading of drug-resistant parasites and the appearance of insecticide-resistant mosquitoes the development of an effective vaccine against the most severe form of malaria caused by *Plasmodium falciparum* is an urgent priority. Vaccine candidates are being targeted against antigens expressed at various stages of the parasite's life cycle (35). The effector mechanisms that may confer immunity to malaria are incompletely understood, but several lines of evidence indicate that antibodies to antigens of asexual blood stage parasites can reduce morbidity and mortality associated with malaria infection. In parasitemic children, for example, passive transfer of antibodies from adults with naturally acquired immunity to malaria has been shown to markedly depress parasite levels (5, 36).

The life cycle of the malaria parasite is complex, encompassing several distinct stages of development. When an infected mosquito bites a human host, malaria parasites are inoculated into the bloodstream as sporozoites which rapidly invade liver cells.

For the next several days the sporozoites undergo massive proliferation within the host liver cells, causing the infected liver cells to rupture and release many thousands of daughter merozoites into the blood stream. The merozoites rapidly target and infect circulating red blood cells (erythrocytes) where they undergo further multiplication. Inside the infected erythrocytes, the merozoites multiply exponentially every few days and burst out to infect other red blood cells. This cyclic and massive increase in parasite burden is responsible for the clinical manifestations of malaria that can lead to severe patient morbidity, if not mortality.

Because infected hepatocytes and erythrocytes release merozoites into the blood stream, the released merozoites are directly accessible to antibodies and effector cells of the immune system before they reinvade erythrocytes. This blood stage exposure makes merozoites a prime target for the development of an antimalarial vaccine, as immune effector cells and antibodies present in the plasma specific for merozoite antigens could block the parasite's invasion of erythrocytes. Several merozoite antigens are thought to be able to induce protective antibodies and are currently considered as vaccine candidate antigens (22). One of the leading candidates is apical membrane antigen 1 (AMA-1), a 83-dDa protein that is synthesized in mature stages of the parasite and is first localized in the neck of the rhoptries, the clubshaped secretory organelles found in the apical end of the parasite (8, 32). Several passive and active immunization studies based on the whole protein have indicated that AMA-1 is involved in eliciting protective immune responses (2, 7, 9, 10, 11, 20, 31, 45), and serves as a target for invasion blocking antibodies (10, 11, 17, 19).

AMA-1 is a type I integral membrane protein with a small transmembrane domain and a large extracellular ectodomain. Protective immune responses raised against full-length AMA-1 have been shown to be directed primarily against conformational epitopes, since reduced and alkylated AMA-1 gives poor protection (2) and is poorly recognized by hyperimmune sera from individuals living in malaria endemic regions (17). Thus, to be effective, a vaccine based on recombinant AMA-1 appears to require proper folding of the protein into its native or near-native structure. While malaria vaccines based on full-length AMA-1 or its ectodomain have been attempted, they suffer from several significant drawbacks. First, AMA-1 is notoriously difficult to produce. AMA-1 production in *E. coli* has been shown to lead to incorrect folding of the protein and thus requires additional steps of purification and refolding that are not suitable for the production of sufficient quantities of pure, clinical grade material. Similarly, production of AMA-1 in eukaryotic host cell expression systems introduces unwanted glycosylation and host-cell derived lipids that require further purification to prevent the heterogeneity of recombinantly produced AMA-1 which would be unacceptable for clinical use.

The production of shorter AMA-1 peptides circumvents many of the problems associated with the production of the full-length ectodomain, as peptides can be synthesized chemically at high yields without host cell contamination. Peptide vaccines based on shorter fragments or subsequences of AMA-1 have been attempted, but a successful peptide-based AMA-1 vaccine has not yet been achieved, due to a variety of unsolved problems. First, the three-dimensional conformation of AMA-1 in solution has yet to be determined, making structure-based peptide design exceedingly difficult. Secondly, peptides covering certain regions of AMA-1 may not comprise any immunogenic epitopes and fail to generate sufficient immune responses. The sufficiency of the immune response generated is significant because the malaria merozoites are exposed to the blood stream for only a short period of time and therefore the clearance of the blood stage parasites requires a vigorous immune response. Lastly, even peptides proven to be highly immunogenic have failed to produce antibodies that inhibit parasite invasion of erythrocytes (2, 37), indicating that the fine specificity of an anti-AMA-1 antibody generated by a candidate peptide subunit vaccine is an important determinant of the efficacy of the subunit vaccine in blocking merozoite invasion. The identification of epitopes capable of generating vigorous growth-inhibitory immune responses against the blood stage malaria parasite thus represents a major advance for the design of peptide-based malaria vaccines.

BRIEF DESCRIPTION OF THE DRAWINGS

FIG. 4 shows the Western blot analysis of the reactivity of anti-AMA49-L1 antisera with *P. falciparum K*1 blood stage lysates as antigen. Sera of all individual mice tested yielded a double band pattern (indicated by arrows) characteristic for the full-length AMA-1 and of its major processing product (83 and 66 kDa, respectively).

DETAILED DESCRIPTION OF THE INVENTION

Figure 1A:
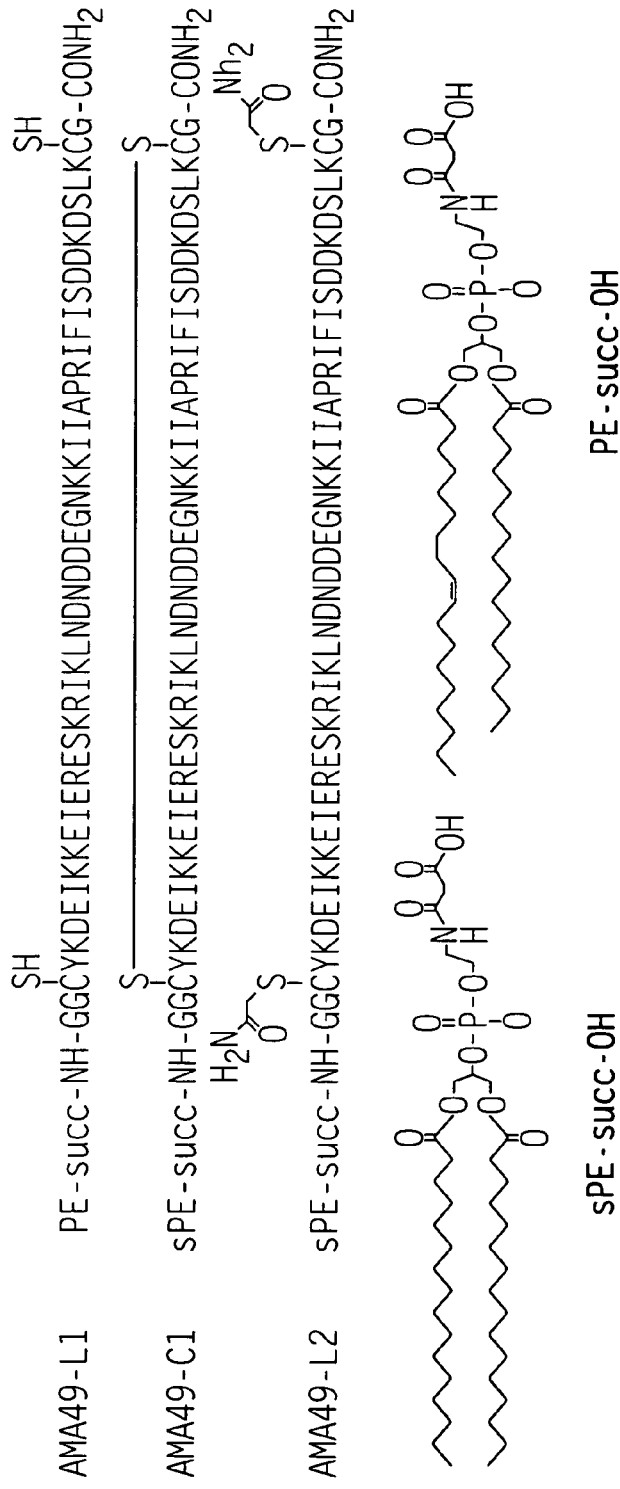
FIGS. 1A and 1B show the structures of the synthetic peptides including AMA49-L1, AMA49-C1 and AMA49-L2, as well as the library of cyclic template-bound peptides each containing 12-residues from AMA-1. The sequences contained within each cyclic peptide are shown in Table-1.

The present invention provides novel compositions and methods for producing effective growth inhibitory immune responses against the blood stage of the malaria parasite. Aspects of the invention are based on the discovery that peptides comprising epitopes present in loop I of domain III of the merozoite protein AMA-1 are surprisingly effective in stimulating vigorous immune responses against AMA-1. The ectodomain of AMA1 comprises a region constituting 16 interspecies conserved cysteine residues which are crosslinked to form eight disulfide bridges. The three-dimensional structure of the AMA-1 protein is stabilized by these eight intramolecular disulfide bonds, which in turn divide the ectodomain into three subdomains (I, II, and III). Previous approaches using the whole AMA-1 ectodomain showed that the majority of antibodies raised against the ectodomain recognize epitopes in domain I, a highly variable region of the protein. However, efforts to design smaller peptide mimetics based on the loop structures in domain I failed to generate protective immune responses, possibly due to the inability of the peptides to accurately mimic the native tertiary structure of the protein (37).

Accordingly, the present invention provides immunostimulatory compositions based on the amino acid sequence of loop I of domain III of AMA-1. By immunostimulatory is meant the ability of the compositions to generate malaria parasite growth inhibitory immune responses. Such immune responses can be humoral or cell-mediated, or both, and their presence and effectiveness can readily be determined by the presence of antibodies that bind to and inhibit the growth of live malaria parasites. In preferred embodiments, the present invention provides epitopes identified in loop I of domain III that are useful for the design of immunostimulatory peptides capable of generating parasite cross-reactive, growth inhibitory immune responses against blood stage malaria merozoites. By epitope is meant that part of the AMA-1 molecule to which T-cell receptors respond or against which a growth inhibitory antibody will be produced and to which it will bind. Such epitopes may be linear, conformational, continuous or discontinuous.

In one preferred embodiment, the present invention provides immunostimulatory compositions comprising the epitopes of SEQ ID NO: 1, 2, 3, or 4, or any combination thereof. The epitopes identified by the present invention can be used by themselves as individual peptides to generate effective immune responses against AMA-1 expressing parasites, or they can be used in combination with each other. In more preferred embodiments, the epitopes form part of a longer peptide, such as that represented by SEQ ID NO: 5, SEQ ID NO: 6, or SEQ ID NO: 7. The epitopes of the present invention, when forming part of a longer peptide (or polypeptide), may be arranged in any orientation or order, including nested or overlapping arrangements, and the peptides containing the diverse arrangements of epitopes may be tested for immunogenicity and immunostimulatory effect by methods well known to persons of skill in the art and as further described herein.

The peptides of the present invention may be produced by chemical synthesis, or they may be of recombinant origin. In addition, their sequences may be modified as long as they retain their immunostimulatory effect, which can be measured by their ability to elicit parasite growth inhibitory immune responses. Thus, in a further preferred embodiment, the invention encompasses functional variants of the peptides of the invention. As used herein, a "functional variant" or "variant" of a peptide is a peptide which contains one or more modifications to the primary amino acid sequence of the peptides of the present invention while retaining the immunostimulatory effect disclosed herein. If a functional variant of a peptide of the present invention involves an amino acid substitution, conservative amino acid substitutions typically will be preferred, i.e., substitutions which retain a property of the original amino acid such as size, charge, hydrophobicity, conformation, etc. Examples of conservative substitutions of amino acids include substitutions made among amino acids within the following groups: (1) M, I, L, V; (2) F, Y, W; (3) K, R, H; (4) A, G; (5) S, T; (6) Q, N; and (7) E, D. Other suitable substitutions are easily established by the person of skill and may additionally be determined by reference to publications such as Voet, *Biochemistry,* Wiley, 1990; Stryer *Biochemistry* 4$^{th}$ Ed., Freeman N.Y., 1995; *Peptide Chemistry. A Practical Textbook,* 2nd ed., Miklos Bodanszky, Springer-Verlag, Berlin, 1993; *Principles of Peptide Synthesis,* 2nd ed., Miklos Bodanszky, Springer-Verlag, Berlin, 1993; *Chemical Approaches to the Synthesis of Peptides and Proteins,* P. Lloyd-Williams, F. Albericio, E. Giralt, CRC Press, Boca Raton, 1997; *Bioorganic Chemistry: Peptides and Proteins,* S. M. Hecht, Ed., Oxford Press, Oxford, 1998, *Synthetic Peptides: A User's Guide,* Gregory A. Grant (Editor), Oxford University Press, 2002, and the like, all of which are incorporated by reference herein.

Methods for identifying functional variants of immunostimulatory peptides of the present invention are provided according to another aspect of the invention. In a first aspect, functional variants of the peptides of the present invention, for example SEQ ID NO: 5, SEQ ID NO: 6 and SEQ ID NO: 7, can be identified by searching the publicly available literature or databases for protein and/or nucleotide sequences for AMA-1 of different *Plasmodium* strains or species. Once the divergent amino acids and their positions are determined, they can be substituted in SEQ ID NO: 5, SEQ ID NO: 6 or SEQ ID NO: 7. For example, D448, K451, and K485 of SEQ ID NO: 5, SEQ ID NO: 6, or SEQ ID NO:7 may be substituted by any amino acid residue of choice, including D448 to N448, K451 to M451, and K485 to I485 to prepare variant peptides. In addition, K473 may be changed to E473 and D484 may be deleted altogether. The numbering of amino acid residues throughout this specification refers to their position in the peptides as depicted in FIG. 1. The ability of the variant peptides to generate or bind to merozoite growth-inhibitory antibodies is then determined, wherein binding to or generating parasite growth inhibitory antibodies comparable to that shown for the original peptides indicates that the variant peptide is a functional variant.

Modifications which generate functional variants of the peptides of the present invention may also comprise the addition of amino acids at either end of the peptides, i.e. at the N or C termini. Again, any well-known method for preparing modified or variant peptides can be employed, such as synthesis of the modified or variant peptide or its recombinant production using a mutated nucleic acid molecule. The peptides of the present invention may also be modified to be more resistant to hydrolysis by proteases, such as by containing D-amino acids or one or more non-hydrolyzable peptide bonds linking amino acids. Non-hydrolyzable peptide bonds are well-known in the art and may include -psi[$CH_2NH$]-reduced amide peptide bonds, -psi[$COCH_2$]-ketomethylene peptide bonds, -psi[CH(CN)NH]-(cyanomethylene)amino peptide bonds, -psi[$CH_2CH(OH)$]-hydroxyethylene peptide bonds, -psi[$CH_2O$] peptide bonds, and -psi[$CH_2S$]-thiomethylene peptide bonds. The peptides of the present invention may also comprise unnatural and unusual amino acids and amino acid analogs, such as ornithine, norleucine, L-malonyltyrosine and others known to those of skill in the art. Alternatively, the peptides of the present invention and their functional variants may be rendered more resistant to degradation or their structural stability may be increased by the inclusion of nonpeptide moities. Preferably, the nonpeptide moieties permit the peptides to retain their natural conformation, or stabilize an optimized bioactive confirmation. Examples of suitable substitutions include D-isomer amino acids, N-methyl amino acids, L-isomer amino acids, modified L-isomer amino acids and cyclized derivatives. Such peptide mimetics can be tested in molecular or cell-based binding assays as described herein to assess the effect of the substitution(s) on conformation and/or activity. Procedures of medicinal chemistry may be applied by one skilled in the art using routine experimental methods of e.g. rational drug design, molecular modeling based on structural information from nuclear magnetic resonance or X-ray diffraction data, and other computational methods. Thus, the invention includes all of the foregoing modifications to the peptides.

In preferred embodiments, the peptides comprise amino acid residues located at or near the termini of the peptides with side chains suitable for the formation of an intramolecular crosslink for purposes of cyclizing the peptides. Suitable residues for crosslinking are well known to a person of skill in the art and may comprise disulfide (cysteine-cysteine), thioether (cysteine-electrophile, such as bromoacetyl, maleimidyl etc.) and other bonds. In a preferred embodiment, the crosslink for cyclization is provided by a disulfide bridge between cysteine residues located at or near the N and C termini of the peptides. In further preferred embodiments, terminal spacer residues are added to the peptides of the invention in order to ensure the spatial accessibility of the crosslinking residues, such as for the incorporation of the cyclic peptide into liposomes, virosomes, or other suitable delivery vehicles. For example, a GGC sequence may be added to the N-terminus and an additional glycine residue at the C-terminus, but many other spacer sequences known to those of skill in the art may be used for the purposes of the present invention, as long as the side chains of the spacer residues are small enough so as not to sterically interfere with the intramolecular crosslink. Examples of suitable spacer residues comprise amino acids such as alanine, serine, asparagine, glutamine, or glycine. Thus, in one preferred embodiment of the invention, the AMA-1 domain III loop I peptides are cyclized by the formation of an intramolecular crosslink. The cyclization of the peptides of the invention provides for the emulation of the native three-dimensional structure of AMA-1 loop I in domain III and is intended to further optimize growth inhibitory immune responses against the parasite. Again, internal crosslinks can be introduced via a number of residues, both natural and synthetic, which are well known in the art. In preferred embodiments terminally positioned (located at or near the N- and C-termini of the peptide) cysteine residues are used to cyclize the peptides through a disulfide bond. An example of such terminally positioned residues for crosslinking is found in SEQ ID NO:6 and SEQ ID NO: 7.

In a further preferred embodiment, the peptides of the present invention and functional variants thereof are cyclized by the use of a template, such as that depicted in FIG. 1. One advantage of using such widely available templates is their rigidity that may stabilize the three-dimensional conformation of the cyclized peptides more effectively than the use of internal crosslinks which typically introduce several rotatable bonds, thereby destabilizing the cyclized peptide structure. Suitable templates for the cyclization of peptide chains are well known in the art and may be tricyclic (Beeli et al., Helvetica Chimica Acta 79: 2235–2248, 1996), diketopiperazine-based (Bisang et al., Helvetica Chimica Acta 79: 1825–1842, 1996), bicyclic, such as a template derived from differentially substituted diaminoprolines (Pfeifer et al., Chem. Commun. 1977–78, 1998) or heterochiral diprolines (Favre et al. J. Am. Chem. Soc. 121: 2679–2685, 1999), to name only a few.

In another preferred embodiment, the present invention provides compositions comprising the AMA-1 domain III loop I peptides either cyclized (template-bound or internally crosslinked) or linear, including functional variants thereof, and a suitable delivery vehicle, such as a liposome or virosome (IRIV). IRIVs (immunostimulatory reconstituted influenza virosomes) are modified liposomes that contain reconstituted fusion-active viral envelope proteins anchored in the phospholipid bilayer. Both liposomes and virosomes are well known adjuvants used in vaccination protocols. Preparation and use of liposomes as adjuvants is standard in the art and described in *The Theory and Practical Application of Adjuvants*, D. E. S. Stewart-Tull (Ed.), Wiley, 1995 and Fries et al., PNAS 89: 358–362, 1992 among many other references. Virosomes can be prepared by detergent removal from a mixture of natural and synthetic phospholipids and influenza surface glycoproteins following protocols well known in the art (34).

The peptides of the invention can be attached to the surface of liposomes or they can be encapsulated by the liposomes using methods such as that described in Christodoulides et al., Microbiology 144: 3027–3037 (1998). Attaching of the peptides of the invention to the surface of delivery vehicles comprises incorporation into, crosslinking or adsorption to the surface of the delivery vehicles, all of which are procedures well known to those of skill in the art. Crosslinking of the peptides to the surface of liposomes, for example, may be performed by the use of amphiphilic PEG derivatives readily incorporated into liposomes and micelles via the PE residue that easily bind primary amino group-containing ligands via water-exposed pNP groups. Similarly, the peptides of the present invention may be encapsulated by virosomes (IRIV), by methods well known in the art and further described in Example 5. Attachment of the peptides to the surface of the virosomes may be performed by any method known to those of skill in the art. In one embodiment of the invention, the peptides of the present invention are attched to virosomes by conjugating the peptides through a succinate linker at the N-terminus to a regioisomer of phosphatidylethanolamine (PE). The PE-peptide conjugate is subsequently incorporated into IRIV as an antigen delivery system.

In a preferred embodiment, the invention provides kits comprising the aforementioned compositions which allow the skilled artisan to prepare a desired immunotherapeutic regimen. An example of a kit comprises the peptides of the invention, as well as their functional variants previously discussed. The kit may also comprise liposomes or virosomes loaded with the peptides of the invention and functional variants thereof, either by encapsulation or by surface-attachment, which includes crosslinking, conjugation and surface-association or -adsorption. In preferred embodiments, a kit provided by the present invention comprises mixtures of liposomes or virosomes encapsulating the peptides of the present invention, including functional variants thereof, with liposomes or virosomes that have the peptides of the present invention, including functional variants therof, attached to their surfaces. Such mixtures may be particularly effective in stimulating various branches of the immune system simultaneously. The kit preferably includes instructions for use of the compositions provided. Other components may be added to the kits, as desired.

Administration of the peptide-loaded virosomes is preferably preceded by one or more pre-immunizations with the empty virosomes or IRIV. Initial doses of the peptide-IRIV delivery system can be followed by booster doses, following immunization protocols standard in the art, and their effect may be potentiated by adjuvants or cytokines well known to those skilled in the art. Again, the peptides of the present invention, as well as functional variants thereof, may be encapsulated by or attached to the surface of the delivery vehicles in linear or cyclized form. The present invention also provides for the administration of the immunostimulatory AMA-1 peptides in a suitable pharmaceutical formulation. By administration or administering is meant providing one or more peptides or peptide-containing compositions of the invention to an individual in need of treatment or prevention of malaria. Such a composition which contains one or more of the peptides and/or peptide containing compositions of the present invention, including functional variants thereof, as the principal or member active ingredient, for use in the treatment or prevention of malaria, can be administered in a wide variety of therapeutic dosage forms in the conventional vehicles for topical, oral, systemic, local, and parenteral administration. Thus, the invention provides compositions for parenteral administration which comprise a solution of the peptides and their functional variants dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Thus, a typical pharmaceutical composition for intradermal infusion could be made up to contain 250 ml of sterile Ringer's solution, and 100 mg of peptide. Actual methods for preparing parenterally administrable compounds will be known or apparent to those skilled in the art and are described in more detail in for example, Remington: The Science and Practice of Pharmacy ("Remington's Pharmaceutical Sciences") Gennaro A R ed. 20th edition, 2000: Williams & Wilkins PA, USA, which is incorporated herein by reference.

The route and regimen of administration will vary depending upon the stage or severity of the malaria to be treated, and is to be determined by the skilled practitioner. For example, the immunostimulatory peptides, including their functional variants, and the peptide-containing compositions of the present invention can be administered in such oral dosage forms for example as tablets, capsules (each including timed release and sustained release formulations), pills, powders, granules, elixirs, tinctures, solutions, suspensions, syrups and emulsions, or by injection. Similarly, they may also be administered in intravenous (either by bolus or infusion methods), intraperitoneal, subcutaneous, topical with or without occlusion, or intramuscular form. In preferred embodiments, the peptides and peptide-containing compositions are administered intradermally or subcutaneously. All of these forms are well known to those of ordinary skill in the pharmaceutical arts.

The daily dose of the peptides and compositions of the invention may be varied over a range from 0.001 to 1,000 mg per adult per day. For oral administration, the compositions are preferably provided in the form of tables containing from 0.001 to 1,000 mg, preferably 0.001, 0.01, 0.05, 0.1, 0.5, 1.0, 2.5, 10.0, 20.0, 50.0, 100.0 milligrams of active ingredient for the symptomatic adjustment of dosage according to signs and symptoms of the patient in the course of treatment. An effective amount of drug is ordinarily supplied at a dosage level of from about 0.0001 mg/kg to about 50 mg/kg of body weight per day. The range is more particular from about 0.0001 mg/kg to 7 mg/kg of body weight per day.

In another preferred embodiment, the peptides of the invention and their functional variants can be administered by injection to a subject in the form of a peptide-based vaccine. Preferably, the peptides are injected intradermally or subcutaneously to allow for uptake by or exposure to antigen presenting cells located in the skin, epidermis or dermis, although other routes of administration known in the art may be equally suitable and are intended to be included in the present invention. In a more preferred embodiment, the peptides of the present invention are loaded, by encapsulation or surface attachment, onto virosomes or liposomes prior to administration to the subject, as described above. The peptide loaded delivery vehicles can then be injected into the subject via intradermal, subcutaneous or other suitable routes analogous to the administration of the peptides described previously. Advantageously, suitable formulations of the present invention may be administered in a single daily dose, or the total daily dosage may be administered in divided doses for example of two, three, or four times daily. The peptides, including functional variants, and compositions of the present invention may be used to prepare a medicament or agent useful for the treatment of malaria. Furthermore, the immunostimulatory compositions of the present invention, particularly those containing virosomes or liposomes, can be administered in intranasal form, or via transdermal routes known to those of ordinary skill in the art.

For the treatment and prevention of malaria the peptides, including functional variants thereof, and compositions of the present invention may be used together with other agents known to be useful in treating malaria. Such agents may include chemotherapeutic drugs, such as quinine, quinidine, chloroquine, mefloquine, tetracycline, mefloxine, halofantrine, artemisinin and derivatives (artemether, artesunate), lumefantrine, doxycycline, proguanil, primaquine, atovaquone-proguanil, pyrimethamine-sulfadoxine etc. For combination treatment with more than one active agent, where the active agents can be administered concurrently, the active agents can be administered concurrently, or they can be administered separately at staggered times.

The dosage regimen utilizing the compositions of the present invention is selected in accordance with a variety of factors, including for example type, species, age, weight, sex and medical condition of the patient, the stage and severity of the malaria infection, and the particular compound employed. A physician of ordinary skill can readily determine and prescribe the effective amount of the drug required to prevent, counter, or arrest the progress of the malaria infection. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, and is within the ability of the skilled practitioner. Guidance as to indications, dosage and drug interactions can further be found in clinical manuals, including Harrison's Principles of Internal Medicine, $15^{th}$ Ed. McGraw-Hill, 2001.

In the methods of the present invention, the compounds herein described in detail can form the active ingredient and are typically administered in admixture with suitable pharmaceutical diluents or excipients suitably selected with respect to the intended form of administration, that is, oral tablets, capsules, elixirs, syrups, and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

The liquid forms may be suitably flavored suspending or dispersing agents such as the synthetic and natural gums, for example, tragacanth, acacia, methyl cellulose and the like. Other dispersing agents which may be employed are glycerin and the like. For parenteral administration, sterile suspensions and solutions are desired. Isotonic preparations which generally contain suitable preservatives are employed when intravenous administration is desired. Topical preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, skin gels, skin lotions, and shampoos in cream or gel formulations.

The immunostimulatory peptides including functional variants thereof and compositions of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels. Generally, subjects can receive an intradermal injection of an effective amount of the peptides either in combination with delivery vectors, such as virosomes, or by themselves. The peptides of the present invention can also be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

Initial doses can be followed by booster doses, following immunization protocols standard in the art. The immunostimulatory effect of the compositions and methods of the instant invention can be further increased by combining any of the above-mentioned peptide compositions, including their combination with virosomes or liposomes, with an immune response potentiating compound. Immune response potentiating compounds are classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include Freund's (complete and incomplete), mycobacteria such as BCG, M. Vaccae, or corynebacterium parvum, quil-saponin mixtures such as QS-21 (SmithKline Beecham), and various oil/water emulsions (e.g. IDEC-AF). Other adjuvants which may be used include, but are not limited to: mineral salts or mineral gels such as aluminum hydroxide, aluminum phosphate, and calcium phosphate; surface active substances such as lysolecithin, pluronic polyols, polyanions, peptides, keyhole limpet hemocyanins, and dinitrophenol; immunostimulatory molecules, such as saponins, muramyl dipeptides and tripeptide derivatives, CpG dinucleotides, CpG oligonucleotides, monophosphoryl Lipid A, and polyphosphazenes; particulate and microparticulate adjuvants, such as emulsions, liposomes, virosomes, cochleates; or immune stimulating complex mucosal adjuvants. Cytokines are also useful in vaccination protocols as a result of lymphocyte stimulatory properties. Many cytokines useful for such purposes will be known to one of ordinary skill in the art, including interleukin-2 (IL-2), IL-12, GM-CSF and many others.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preparations of the invention are administered in effective amounts. An effective amount is that amount of a pharmaceutical preparation that alone, or together with further doses, stimulates the desired response. Generally, doses of immunogens ranging from one nanogram/kilogram to 100 miligrams/kilogram, depending upon the mode of administration, are considered effective. The preferred range is believed to be between 500 nanograms and 500 micrograms per kilogram. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be addressed with no more than routine experimentation.

In further preferred embodiments, the present invention provides methods of generating parasite growth inhibitory immune responses comprising administering to a subject the peptides, including functional variants thereof, and compositions of the invention. In the case of treating malaria, the desired response is inhibiting the progression of the infection, reducing the parasitic load, and/or clearance of the parasite from the subject. In the case of preventing malaria, the desired response is the induction of vigorous antibody- and/or cell mediated immune responses against AMA-1 expressing parasites. These desired responses can be monitored by routine methods or can be monitored according to diagnostic methods of the invention disclosed herein. The present invention is not to be limited in scope by the specific embodiments described herein. Indeed, various modifications of the invention in addition to those described herein will become apparent to those skilled in the art from the foregoing description, as well as from the examples. Such modifications are intended to fall within the scope of the appended claims.

Results

The present invention demonstrates for the first time that it is possible to elicit parasite growth inhibitory antibodies with formulations of peptides comprising epitopes found in loop I of domain III of *P. falciparum* AMA-1. The development of peptide based vaccines has been hampered both by the poor immunogenicity of many peptides, possibly due in part to a lack of conformational similarity between small linear peptides and the corresponding sequence in the native target protein. Accordingly, the present invention provides immunostimulatory peptides comprising newly identified immunogenic epitopes that can be combined with human compatible delivery systems, including virosomes (IRIVs) and/or liposomes. The peptides of the invention can be encapsulated by, or attached to, the delivery vehicles for the efficient generation of AMA-1 specific immune responses. IRIVs, or virosomes, are spherical, unilammelar vesicles, prepared by detergent removal from a mixture of natural and synthetic phospholipids and influenza surface glycoproteins. They have been shown to act as an efficient and highly effective means of enhancing the immune response to a variety of antigens, thus illustrating their broad suitability as a vaccine delivery system (14). The hemagglutinin membrane glycoprotein of influenza virus plays an important role in the mode of action of IRIVs. This major antigen of influenza virus is a fusion-inducing component, which facilitates antigen delivery to immunocompetent cells. In the case of the IRIV-based hepatitis A vaccine Epaxal-Bema, which is the first licensed vaccine in which IRIVs are used as a delivery system for a non-influenza antigen, the hepatitis A antigen spontaneously binds to the IRIVs, thus attaching to the delivery vehicles. Smaller antigens, including the peptides of the present invention can be linked to a phospholipid (PE) and the PE-antigen conjugates can be integrated into the virosomal membrane during the virosome reconstitution process (28, 34).

Compared to a virosome formulation loaded with a PE conjugate of a cyclic peptide mimotope of the repeat region of the *P. falciparum* circumsporozoite protein, an alum-adjuvanted mimotope-MAP (multiple antigenic peptide) construct, although capable of eliciting comparable levels of anti-mimotope antibody responses in mice, failed to produce antibodies that bind effectively to the parasites, indicating that PE-coupled antigens are located in a more native-like state on the surface of the virosomes. These results may indicate that intramolecular interactions lead to a correct folding of the linear peptide and that the anchoring to the surface of IRIVs has no deleterious effects on this process. The solution structure of the AMA-1 domain III, determined by NMR spectroscopy, consists of a disulfide-stabilized core region including all three disulfide bonds, but also contains significant regions of disorder (29). The epitope analysis of growth inhibitory anti-AMA49 MAbs using a library of 12-residue cyclic peptides covering the AMA$^{444-489}$ sequence (FIG. 1) performed herein provides evidence that at least some of the MAbs may recognize discontinuous epitopes. Since discontinuous epitopes may contain short stretches of continuous sequences (1, 3, 38), analyses with sets of overlapping peptides are suitable to define both continuous linear epitopes and parts of discontinuous epitopes (15, 41). The analyses indicate that $K^{459}RIKLN^{464}$ (SEQ ID NO: 1) and $D^{467}DEGNKKII^{475}$ (SEQ ID NO: 2) represent sequence stretches of discontinuous epitopes recognized by inhibitory anti-AMA-1 MAbs.

AMA-1 lacks tandem repeat sequences found in many other *P. falciparum* antigens. However, a significant degree of sequence diversity is observed, which may reflect diversifying selection pressure. from naturally acquired immune responses (9, 13, 33, 42). Most of the polymorphic or dimorphic amino acid residues of the relatively conserved domain III are located far apart from each other in the primary sequence, but may cluster in the region of the disulphide core in the three-dimensional structure of the molecule (29). This is also the case for the three variable residues ($D^{448}$, $K^{451}$ and $K^{485}$) present in the AMA-1$^{446-490}$ sequence analyzed herein. The virosomal formulation of this peptide seems to focus the antibody response primarily to conserved loop structures away from this core region. Cross protection obtained with antibodies raised against recombinantly expressed AMA-1 has provided evidence for the existence of such common protective epitopes (17, 21). Taken together, these results indicate that the loop I sequence from domain III of AMA-1 represents a suitable component of an IRIV-based multi-antigen multi-stage synthetic peptide malaria vaccine candidate.

Accordingly, a sequence comprising 45 amino acid residues from loop-I in domain III of AMA-1, $Y^{446}$KDEIKKEI-ERESKRIKLNDNDDEGNKKIIAPRIFISDDKDSLKC$^{490}$ (SEQ ID NO: 5) with a GGC sequence added to the N-terminus and an additional glycine residue at the C-terminus was synthesized by standard solid phase peptide chemistry. In order to load the peptide onto virosomes, it was conjugated through a succinate linker at the N-terminus to a regioisomer of phosphatidylethanolamine (PE) and the PE-peptide conjugate designated AMA49-L1 (FIG. 1, L standing for the linear form) was incorporated into IRIV as antigen delivery system. After one pre-immunization with the influenza vaccine Inflexal, mice were immunized with AMA49-L1 loaded IRIV. All four mice immunized produced antibodies that reacted with AMA49-L1 in ELISA (FIG. 2).

Figures 4, 5A:
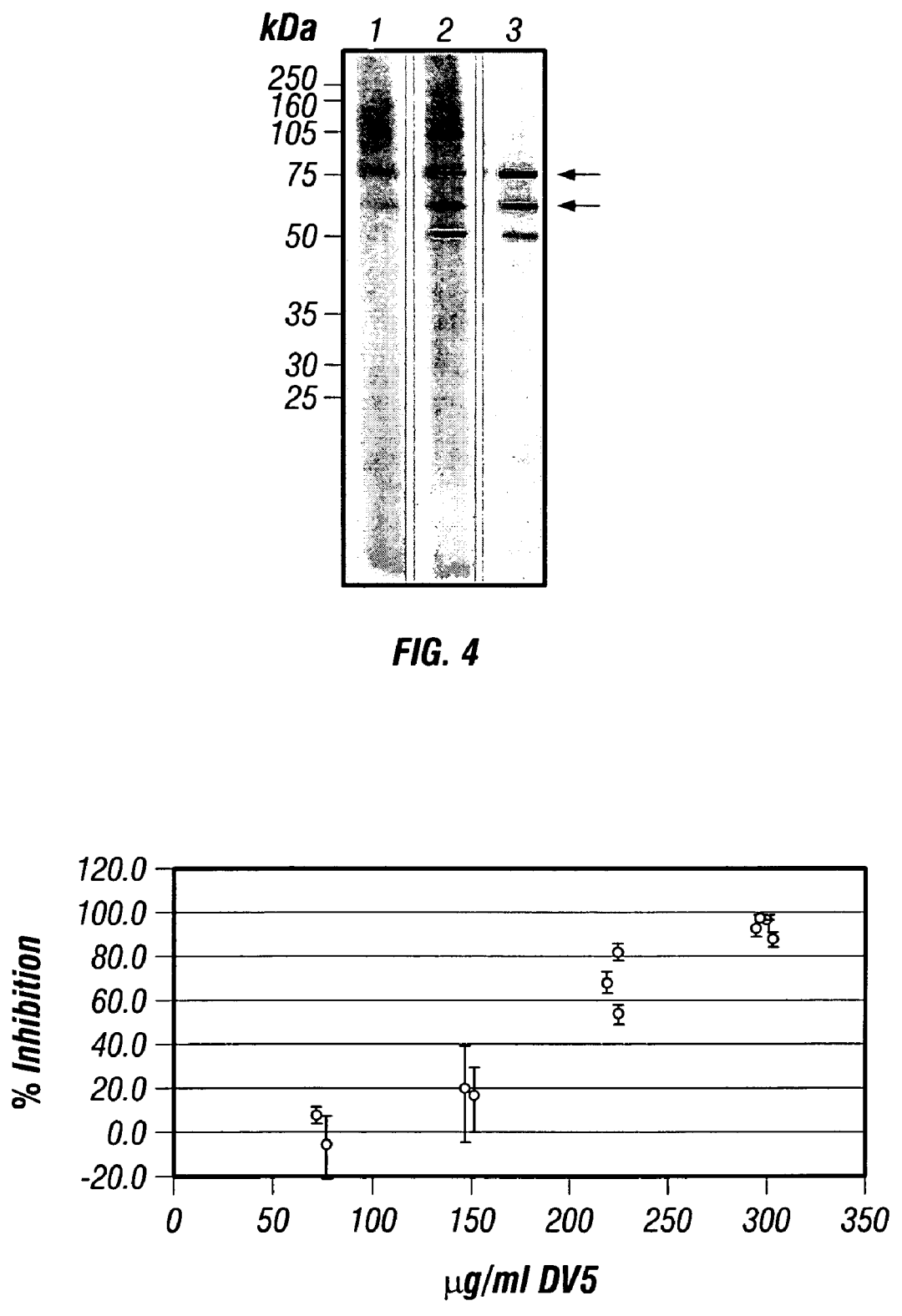

The elicited antibodies were cross-reactive with blood stage parasites in IFA (FIG. 3), yielding a punctate staining pattern characteristic for AMA-1 (17, 27). Interaction of mouse anti-AMA49-L1 sera with parasite expressed AMA-1 was re-confirmed by Western blot analysis using total protein lysates of *P. falciparum* blood stage parasites (FIG. 4). The anti-AMA49-L1 antisera stained primarily proteins of an apparent molecular mass of approximately 83 and 66 kDa, which is the size of the full-length AMA-1 and of its major processed product, respectively (17, 30). Some of the anti-AMA49-L1 antisera stained an additional protein band, which may correspond to the previously described 46 kDa processing product of AMA-1 (18) that possesses the same N-terminus as the 66 kDa fragment.

Figure 1B:
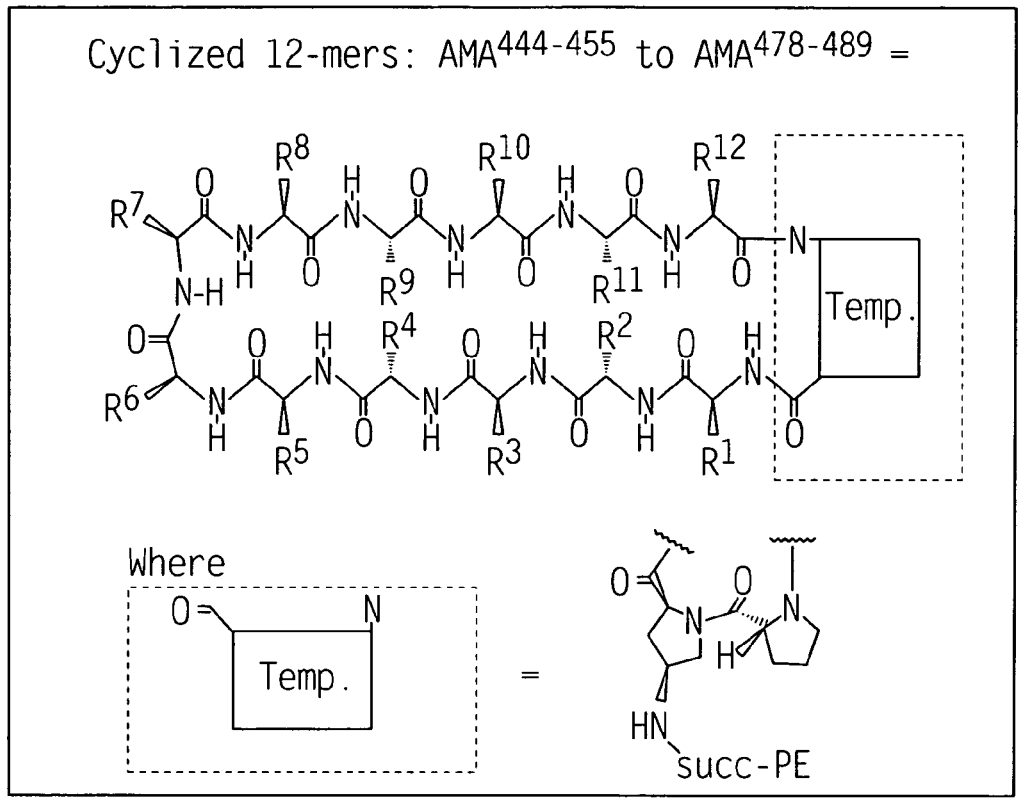
Figure 2:
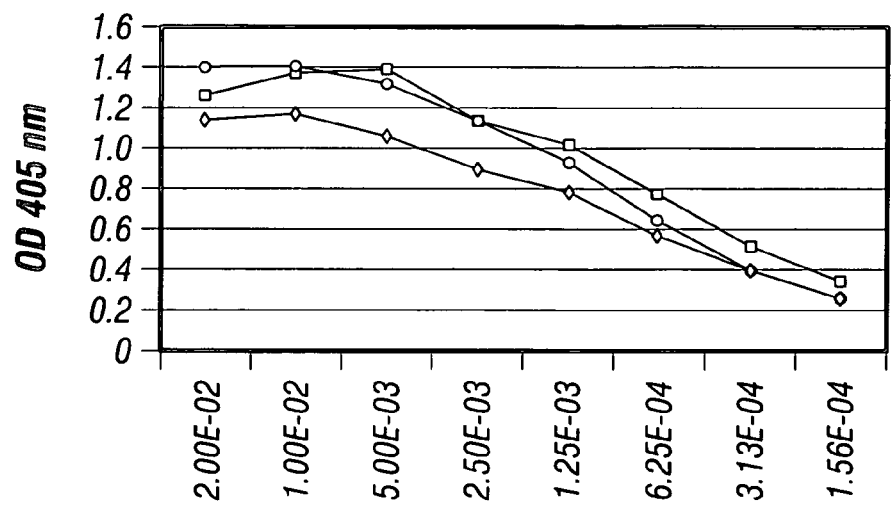
FIG. 2 shows the AMA49-L1 specific IgG ELISA titers after three immunizations of mice with AMA49-L1-loaded IRIV. Responses of individual mice are shown. Their preimmune sera showed no significant reactivity with AMA49-L1 (data not shown).
Figure 3A:
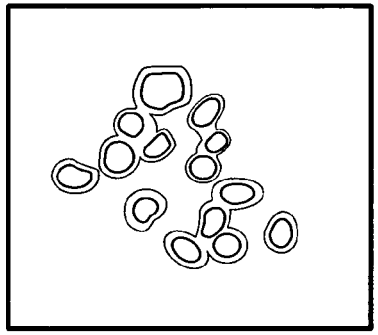
FIGS. 3A and 3C show the parasite DNA control staining with preimmune serum (diluted 1:100).
Figure 3B:
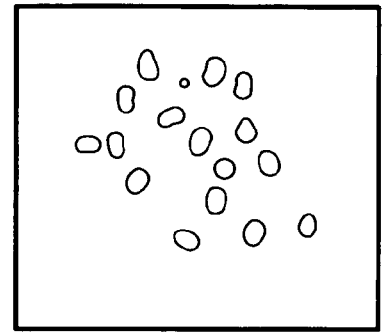
FIG. 3B shows AMA-1 characteristic immunostaining of mature schizonts of *P. falcivarum* strain K1 by antibodies elicited by AMA49-L1-loaded IRIV.
Figure 3C:
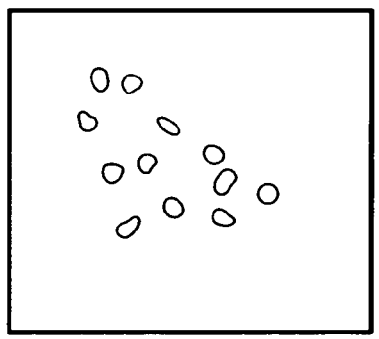
Figure 3D:
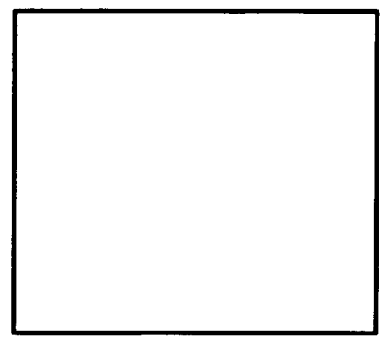
FIG. 3D shows the lack of staining with pre-immune serum. Representative results with sera of one of the immunized mice are shown. All other AMA49-L 1 immunized mice showed comparable IFA-reactivities.

In order to investigate whether cyclization of the peptide via the cysteine residues close to the C- and N-termini improves the yield of parasite binding antibodies, mice were immunized with IRIV loaded with a cyclized (AMA49-C1) and a linear (AMA49-L2) version of AMA49-L1 (FIG. 1). While AMA49-L1 contained free thiols, both thiol groups of the terminal cysteine residues were blocked by alkylation in the case of AMA49-L2. IFA titers obtained with the two constructs did not differ significantly and were comparable to those obtained with AMA49-L1 (data not shown).

For a detailed analysis of the humoral immune response, AMA49-C1 specific mouse B cell hybridomas were generated. All 11 hybridoma clones obtained secreted IgG:κ (10 MAbs were IgG1, MAb DV3 was IgG2a) that reacted in ELISA both with the cyclic and the linear peptide with comparable efficacy. These 11 MAbs all stained blood stage parasites in IFA (data not shown). Competition ELISA experiments with a set of 4 overlapping linear peptides comprising the sequences $AMA^{446-462}$, $AMA^{452-472}$, $AMA^{462-482}$, and $AMA^{472-490}$ FIG. 1) were used for epitope mapping and differentiated between four groups of antibodies (Table 2).

Antigen binding of MAbs DV2 and DV6 was blocked by $AMA^{446-462}$, MAb DV7 was blocked both by $AMA^{446-462}$ and $AMA^{452-472}$, MAbs DV5 and DV8 were blocked by $AMA^{452-472}$ and MAbs DV1, DV3, DV4, DV9, DV10 and DV11 were blocked by $AMA^{462-482}$. None of the antibodies was blocked by the C-terminal sequence $AMA^{472-490}$. A library of 35 cyclic peptides each containing 12 residues scanning the $AMA^{444-489}$ sequence each with an offset of one amino acid, was used for more detailed epitope mapping (see FIG. 1 and Table.2). These peptides were conformationally restrained by cyclization through linkage to a dipeptide template comprising a D-proline and an L-4-aminoproline conjugated to succPE. In ELISA, both MAbs DV2 and DV6 inhibited by $AMA^{446-462}$ bound to none of the short cyclic peptides. MAb DV7 bound to the consecutive cyclic peptides comprising residues 450–461 through 455–466, which share the sequence $E^{455}RESKRI^{461}$ (SEQ ID NO: 3) present also in the overlap of the two inhibitory long peptides $AMA^{446-462}$ and $AMA^{452-472}$. MAbs DV5 and DV8 bound to cyclic peptides 453–464 through 459–470, which share the sequence $K^{459}RIKLN^{464}$ (SEQ ID NO: 1) located in the center of the inhibitory peptide $AMA^{452-472}$. Additional binding of both MAbs to the non-consecutive cyclic peptide 477–488 and of MAb DV5 to cyclic peptide 474–485 is indicative of a discontinuous epitope. All six MAbs that were inhibited by $AMA^{462-482}$ exhibited binding to the consecutive peptides 464–475 through 467–478 which share the sequence $D^{467}DEGNKKII^{475}$ (SEQ ID NO: 2) located in the centre of the inhibitory long peptide $AMA^{462-482}$. MAb DV1 reacted in addition with the overlapping peptide 462–473. In the case of MAb DV3 the reactivity with peptide $N^{466}DDEGNKKIIAP^{477}$ (SEQ ID NO: 8) was outstanding. With the other four MAbs DV4, DV9, DV10 and DV11 reactivity patterns with non-overlapping peptides indicate recognition of a discontinuous epitope. All four MAbs showed reactivity with the peptide 456–67, which only overlaps at position $D^{467}$ with the putative central $D^{467}DEGNKKII^{475}$ (SEQ ID NO: 2) recognition sequence. In addition, MAbs DV4 and DV9 also bound to the non-consecutive peptides 474–485 and 478–489 and to the peptides 462–473, 463–474 which share the sequence $D^{467}DEGNKK^{473}$ (SEQ ID NO: 9) with the central recognition sequence.

Mice were immunized with IRIV loaded with PE conjugates of each of the cyclic 12-mer peptides in order to analyze whether some of them can act as mimotopes of AMA-1 surface loops and elicit parasite-binding antibodies. While all 35 structures elicited significant antibody titers against the respective immunizing peptide sequence itself, only sera raised against $AMA^{458-469}$ (containing the central recognition unit $K^{459}RIKLN^{464}$ (SEQ ID NO: 1) of MAbs DV5 and DV8) and $AMA^{464-475}$ (containing the central recognition unit $D^{467}DEGNKKII^{475}$ (SEQ ID NO: 2) of MAbs DV1, DV3, DV4, DV9, DV10 and DV11) were weakly cross-reactive with blood stage parasites in IFA (data not shown).

Figure 5B:
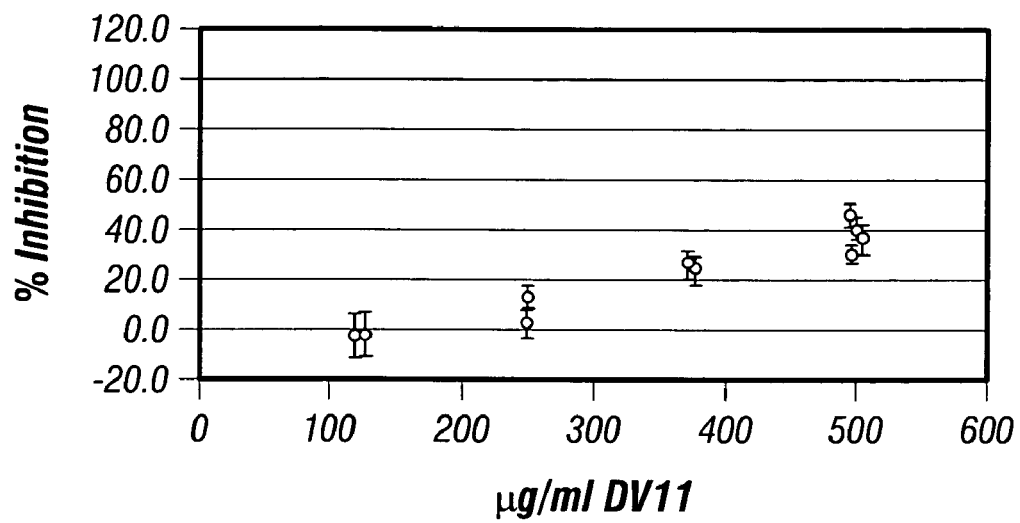
FIGS. 5A, B and C show the parasite in vitro growth inhibitory activity of anti-AMA49 MAbs. A: MAb DV5; B: MAb DV11; C: isotype-matched control antibodies. Each symbol represents the mean of an independent sixtuplicated experiment and error bars indicate the 95% CI (P<0,05, two-sided t test).
Figure 5C:
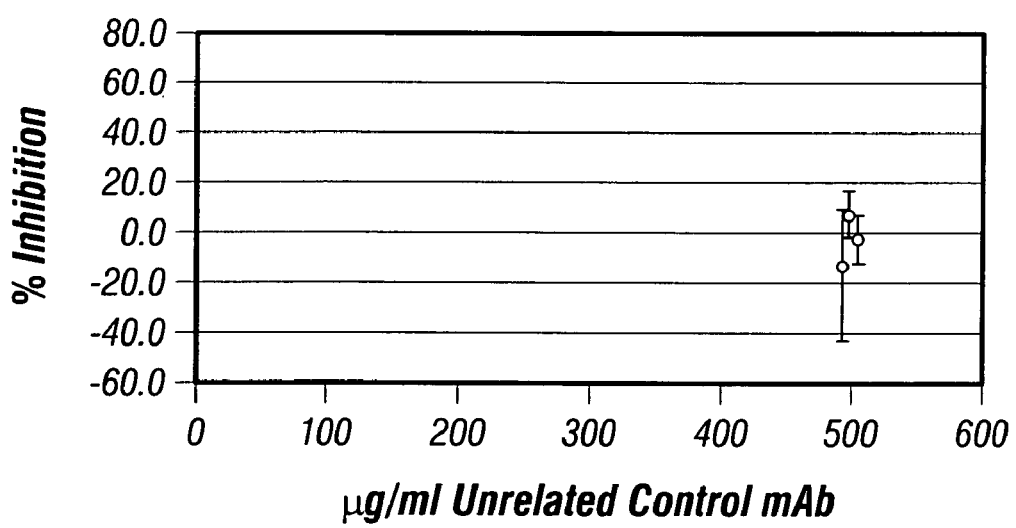

When Mabs DV5 and DV11 representing the two major fine specificities were tested in a *P. falciparum* in vitro growth inhibition assay, both exhibited substantial inhibitory activity (FIG. 5). A 95.3% reduction of parasite growth was observed after addition of MAb DV5 at a final concentration of 300 µg/ml (average of five independent sixtuplicated experiments). MAb DV11 also exhibited a significant, but lower growth inhibitory activity, while an isotype-matched control MAb had no effect. Taken together, these data clearly demonstrate that it is possible to elicit parasite binding and growth inhibitory antibodies by immunization with $AMA-1^{446-490}$ in combination with IRIV as a human compatible antigen delivery system.

AMA-1 is a leading malaria blood-stage vaccine candidate, which has been shown to elicit protective immune responses when administered as a whole protein. Parasite invasion inhibitory activities of anti-AMA-1 antibodies indicate that the humoral arm of the immune response plays an important role in AMA-1 mediated immune protection. The ectodomain of AMA-1 is divided into three sub-domains defined by disulfide bonds (16). There is evidence that the majority of inhibitory antibodies in sera from malaria exposed humans and in rabbit antisera raised against the refolded AMA-1 ectodomain are directed against strain-specific epitopes in domain I (17). An analysis of tryptic fragments of *P. chabaudi adami* AMA-1 recently identified a loop-like structure within the putative domain I as a target of antibodies from hyperimmune mouse sera (37). A synthetic 45mer loop mimetic incorporating this element was found to elicit AMA-1 binding antibodies. However, these antibodies did not protect *P. chabaudi adami* challenged mice in passive immunization experiments. Since domain I is the most diverse region of AMA-1 (25, 46), an AMA-1 vaccine component which lacks this domain may be preferable in order to direct the immune response to region(s) that contain more conserved epitopes (17). Since production of large batches of clinical-grade recombinantly expressed AMA-1 has been notoriously difficult, the present invention is directed to the development of a synthetic peptide-based AMA-1 vaccine formulation. The results obtained by the present invention show that it is possible to elicit parasite growth inhibitory antibodies with a virosomal formulation of peptides comprising parts of the sequence of loop I from domain III of *P. falciparum* AMA-1.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

The following abbreviations are used herein: AMA-1, apical membrane antigen 1; ELISA, enzyme-linked immunosorbent assay; IFA, indirect immunfluorescence assay; Ig, immunoglobuline; IRIV(s), immunopotentiating reconstituted influenza virosome(s); MAb(s), monoclonal antibody(ies); MSP-1, merozoite surface protein 1; *P. falciparum*, Plasmodium falciparum; PE, phosphatidylethanolamine; SDS-PAGE, sodium dodecyl sulfate-polyacrylamide gel electrophoresis.

Example 1

This example shows the design and synthesis of a linear peptide based on loop 1 of domain III of AMA-1. A 49 residue peptide comprising residues AMA-1446–490, with three additional amino acids (GGC) at the N-terminus, and one additional G residue at the C-terminus (FIG. 1), was prepared by solid phase peptide synthesis on Sieber amide resin (0.5 mmol/g) using Fmoc chemistry and an ABI433A peptide synthesizer. The pseudoproline unit Fmoc-IleSer ($\psi^{Me,Me}$pro)-OH was used in place of Ile39 and Ser40. After assembly, the peptide was cleaved from a portion of the resin using TFA:H$_2$O:EDT:TIS (92.5:2.5:2.5:2.5) for 3.5 h at room temperature. After concentration in vacuo the peptide was precipitated with diethyl ether, and purified by reverse-phase HPLC (C18 column) using a gradient of MeCN in water (25% to 50%) with 0.1% TFA over 15 min. The purity was >95% by analytical HPLC. The constitution was confirmed by amino acid analysis and electrospray mass spectrometry (Table-1). Another portion of the resin carrying the intact peptide chain (ca. 60 μmol) was treated with PE-succ-OH (130 mg, 160 μmol) (FIG. 1), HATU (61 mg, 160 μmol), HOAt (22 mg, 160 μmol), and iPr2EtN (82 μl) in DMF:CH$_2$Cl$_2$ (4 ml, 1:2) for 18 h at room temp. After washing the resin with DMF (4×) and CH2Cl2(4×) the peptide conjugate was cleaved from the resin with 1% TFA in CH$_2$Cl$_2$ (4×4 ml). The combined organic fractions were concentrated in vacuo and the conjugate was redissolved in TFA:H2O:EDT:TIS (92.5:2.5:2.5:2.5) for 4 h at room temp. The TFA was then removed in vacuo and AMA49-L1was precipitated with iPr2O and then purified by HPLC on a C4 column using a gradient of 10 to 100% MeCN/water with 0.1% TFA. The purity was >95% by analytical HPLC. The constitution was confirmed by amino acid analysis and electrospray mass spectrometry (Table-1). The presence of two free thiols was proven by an Ellman test, and by reaction with excess N-ethylmaleimide (NEM) and detection of the bis-NEM derivative by HPLC-MS. AMA49-C1 was prepared in the same way except that sPE-succ-OH was used (FIG. 1), and in the final step the conjugate (4 mg) was oxidized in ammonium acetate buffer (50 mM, pH 8) and 2,2,2-trifluoroethanol (TFE) (1:1, 100 ml) for 4 days at room temperature. After addition of AcOH (100 μl) and lyophilization, AMA49-C1 was purified by HPLC as above for AMA49-L1. The formation of the disulfide bridge was confirmed by a negative Ellman test and by attempted derivatization with NEM, which gave no bis NEM-derivative by HPLC-MS. For the synthesis of AMA49-L2, the dithiol (6 mg) was alkylated with iodoacetamide (43μmol) in a mixture (5:4) of phosphate buffer (0.1 M, pH 7.5) and TFE. The AMA49-L2 was purified by HPLC on a C4 column using a gradient of 10 to 100% MeCN/water with 0.1% TFA. The purity was >95% by analytical HPLC. Electrospray mass spectrometry showed the expected mass (Table 1).

TABLE 1

Mass spectrometric characterization of peptides synthesized

| Peptide Sequence | Calculated Mass | Measured Mass (m/z) |
|---|---|---|
| AMA-1$^{446-490}$ | 5625.4 | 1125.9 [M + 5H]$^{5+}$, 938.9 [M + 6H]$^{6+}$, 804.6 [M + 7H]$^{7+}$, 704.4 [M + 8H]$^{8+}$. |
| AMA-1$^{446-462}$ | 2408.8 | 1204.7 [M + 2H]$^{2+}$, 803.8 [M + 3H]$^{3+}$, 603.0 [M + 4H]$^{4+}$ |
| AMA-1$^{452-472}$ | 2529.8 | 1265.5 [M + 2H]$^{2+}$, 844.5 [M + 3H]$^{3+}$, 633.4 [M + 4H]$^{4+}$ |
| AMA-1$^{462-482}$ | 2400.7 | 1200.7 [M + 2H]$^{2+}$, 800.8 [M + 3H]$^{3+}$ |
| AMA-1$^{467-490}$ | 2246.7 | 1124.1 [M + 2H]$^{2+}$, 749.8 [M + 3H]$^{3+}$ |
| AMA49-L1 | 6425.4 | 1607.5 [M + 4H]$^{4+}$, 1285.8 [M + 5H]$^{5+}$, 1071.9 [M + 6H]$^{6+}$, 918.9 [M + 7H]$^{7+}$ |
| AMA49-C1 | 6396.4 | 1280.2 [M + 5H]$^{5+}$, 1067.0 [M + 6H]$^{6+}$, 914.8 [M + 7H]$^{7+}$ |
| AMA49-L2 | 6512.3 | 1303.4 [M + 5H]$^{5+}$, 1086.4 [M + 6H]$^{6+}$, 931.4 [M + 7H]$^{7+}$, 815.0 [M + 8H]$^{8+}$, 724.6 [M + 9H]$^{9+}$ |

Electrospray mass spectra were recorded on a Bruker Esquire-LC-MS or using a Finnegan-TSQ-700 spectrometer Example 2

This example shows the production of linear peptides AMA1$^{446-462}$, AMA1$^{452-472}$, AMA1$^{462-482}$, and AMA1$^{467-490}$ and of a library of 35 12 mer cyclic peptides, which scan the AMA$^{444-489}$ sequence for epitope mapping of loop I. AMA1$^{446-462}$, AMA1$^{452-472}$, AMA1$^{462-482}$, and AMA1$^{467-490}$ were prepared by standard Fmoc solid-phase peptide synthesis (Example 1), purified by reverse phase HPLC on a C18 column and a gradient of MeCN in water with 0.1% TFA, and characterized by amino acid analysis and electrospray mass spectrometry (Table 1).

A library of 35 12 mer cyclic peptides, which scan the AMA$^{444-489}$ sequence (FIG. 1 and Table-2) was prepared. Each mimetic was ≧95% pure by HPLC and the structure was confirmed by electrospray mass spectrometry. The primary structure of all synthesized peptides was based on the AMA-1 domain-III sequence of the *P. falciparum* strain K1 (accession number U33279).

Example 3

This example shows the preparation of peptide-loaded virosomes wherein the peptides are incorporated into the virosome surface. For the preparation of PE-mimetic-IRIV, a solution of purified Influenza A/Singapore hemagglutinin (4 mg) in phosphate buffered saline (PBS) was centrifuged for 30 min at 100 000 g and the pellet was dissolved in PBS (1.33 ml) containing 100 mM octaethyleneglycolmonodecyether (PBS-OEG). Peptide-PE conjugates (4 mg), phosphatidylcholine (32 mg; Lipoid, Ludwigshafen, Germany) and phosphatidyletnanolamine (6 mg) were dissolved in a total volume of 2.66 ml of PBS-OEG. The phospholipid and the hemagglutinin solutions were mixed and sonicated for 1 min. This solution was then centrifuged for 1 hour at 100 000 g and the supernatant was filtered (0.22 µm) under sterile conditions. Virosomes were then formed by detergent removal using BioRad SM BioBeads (BioRad, Glattbrugg, Switzerland).

Example 4

This example shows how the crosslinking of peptides to IRIVs is performed. Phosphatidylethanolamine PE was dissolved in methanol and 0.1% (v/v) triethylamine was added. The solution was then mixed with the heterobifunctional crosslinker N-☐-maleimidobutyryloxy-succimide-ester (GMBS), (Pierce Chemical Company, Rockford, Ill.) (ratio PE:GMBS=5:1), which was previously dissolved in dimethylsulfoxide (DMSO) (20 ☐l). After incubation during 30 minutes at room temperature, the solvents were evaporated for 1 h under vacuum in a speedvac centrifuge. The GMBS-PE was then dissolved in 1 ml of PBS containing 100 mM octaethyleneglycol (OEG) (Fluka Chemicals, Switzerland), (PBS-OEG) and the peptide was added (ration PE-GMBS: peptide=5:1). In this step, the phosphatidylethanolamine-GMBS react with a free cystein of the peptide. After in incubation time of 30 minutes, free cystein was added, in order to inactivate free GMBS (ratio Cystein:GMBS=10:1).

32 mg egg phosphatidylcholine (PC), (Lipoid GmbH, Ludwigshafen, Germany) and 6 mg phosphatidylethanolamine(PE), (R. Berchtold, Biochemisches Labor, Bern, Switzerland) were dissolved in 2.66 ml of PBS containing 100 mM octaethyleneglycol (OEG) (Fluka Chemicals, Switzerland), (PBS-OEG). The influenza A/Singapore hemagglutinin was purified as described previously [16]. A solution containing 4 mg hemagglutinin was centrifuged for 30 min at 100,000 g and the pellet was dissolved in 1.33 ml of PBS-OEG. The peptide-GMBS-PE construdt and phospholipids were added to the hemagglutinin-solution, well mixed and sonicated for 1 min. This mixture was then centrifuged for 1 h at 100,000 g and the supernatant sterile filtered (0.22 mm). Virosomes were then formed by detergent removal using BioRad SM Bio-Beads.

Example 5

This example shows the encapsulation of peptides into IRIVs.32mg egg phosphatidylcholine (PC), (Lipoid GmbH, Ludwigshafen, Germany) and 6 mg phosphatidylethanolamine(PE), (R. Berchtold, Biochemisches Labor, Bern, Switzerland) were dissolved in 2.66 ml of PBS containing 100 mM octaethyleneglycol (OEG) (Fluka Chemicals, Switzerland), (PBS-OEG). The influenza A/Singapore hemagglutinin was purified as described previously [J. J. Skehel, G. C. Schild, *The polypeptide composition of influenza A viruses*. Virology 44 (1971)396–408].

A solution containing 4 mg hemagglutinin was centrifuged for 30 min at 100,000 g and the pellet was dissolved in 1.33 ml of PBS-OEG. The lipophilic peptide and phospholipids were added to the hemagglutinin-solution, well mixed and sonicated for 1 min. This mixture was then centrifuged for 1 h at 100,000 g and the supernatant sterile filtered (0.22 mm). Virosomes were then formed by detergent removal using BioRad SM Bio-Beads.

Example 6

This example shows the immunogenicity studies of the peptide-loaded virosomes in mice and ELISA analyses. BALB/c mice were pre-immunized intramuscularly with 0.1 ml of the commercial whole virus influenza vaccine Inflexal Berna™ (Berna Biotech, Bern, Switzerland). At least three weeks later they were immunized with peptide-loaded IRIVs in intervals of at least two weeks. Blood was collected before each immunization and two weeks after the final injection.

ELISA analyses with peptide-PE conjugates were performed essentially as described (28). Briefly, Polysorp™ plates (Nunc, Fisher Scientific, Wohlen, Switzerland) were coated overnight at 4° C. with 100 μl of a 10 μg/ml solution of AMA-1 peptide-PE conjugate in PBS (pH 7.2). Wells were then blocked with 5% milk powder in PBS for 30 min at 37° C. followed by three washings with PBS containing 0.05% Tween-20. Plates were then incubated with serial dilutions of anti-mimetic mouse sera or anti-AMA49-L1 monoclonal antibodies (MAbs) in PBS containing 0.05% Tween-20 and 0.5% milk powder for 2 h at 37° C. After washing, plates were incubated with alkaline phosphatase-conjugated goat anti-mouse γ heavy chain antibodies (Sigma, St. Louis, Mo.) for 1 h at 37° C. After washing again, phosphatase substrate solution (1 mg/ml p-nitrophenyl phosphate [Sigma] in a pH 9.8 buffer solution containing 10% [vol/vol] diethanolamine and 0.02% $MgCl_2$) was added and the plates were incubated in the dark at room temperature until the colorimetric reaction had progressed sufficiently. The optical density was measured at 405 nm on a Titertek Multiscan MCC/340 reader (Labsystems, Helsinki, Finnland). In competition assays, peptide-PE coated plates were incubated for 2 hours with MAbs in the presence of increasing concentrations of competitor peptides. Isotypes of anti-AMA49 MAbs were determined by detecting MAbs bound to peptide-PE coated plates with alkaline phosphatase conjugated goat antibodies specific for mouse Ig $\gamma_1$, $\gamma_{2a}$, $\gamma_{2b}$, $\gamma_3$, κ or λ chains (Southern Biotechnology, Birmingham, Ala.).

Example 7

This example shows how the indirect immunofluorescence assays (IFA) were performed. Multi-well immunofluorescence microscopy slides (Flow Laboratories, Baar, Switzerland) were pretreated with 0.01% poly-L-lysine (Sigma) at room temperature for 30 min and washed five times with RPMI basal salt medium (Gibco BRL, Basel, Switzerland). Erythrocytes from in vitro cultures (26) of *P. falciparum* strain K1 with a parasitemia between 5-10% were washed twice in RPMI, resuspended in RPMI and two volumes of a solution containing 4% formaldehyde and 0.1% Triton X-100. From this cell suspension, 30 μ were added to each well, incubated at room temperature for 30 min and washed five times with PBS. Wells were incubated for 30 min at room temperature with blocking solution containing 1% fatty acid-free bovine serum albumin (BSA) in PBS. Immunostaining was performed by incubating the wells with 25 μl of an appropriate antibody or serum dilution in blocking solution in a humid chamber for 1 h at room temperature. After five washes with blocking solution 25 μl of 5 μg/ml cyanine dye (Cy3)-conjugated affinity-pure $F(ab')_2$ fragment goat anti-mouse Ig γ heavy chain antibodies (Jackson Immuno Research Laboratories, West Grove, Pa.), diluted in blocking solution containing 0.01 mg/ml Hoechst dye no. 33256 (Sigma) were added to the wells and incubated for 1 h at room temperature. Finally, wells were washed five times, mounted with mounting solution (90% [vol/vol] glycerol containing 0.1 M Tris-Cl, pH 8.0 and 2 mg/ml o-phenylenediamine) and covered with a coverslip. Antibody binding and DNA staining were assessed by fluorescence microscopy on a Leitz Dialux 20 fluorescence microscope and documented with a Leica DC200 digital camera system.

Example 8

This example demonstrates how the SDS-PAGE and immunoblotting assays were performed. Parasite lysates were prepared essentially as described (26) by saponin lysis of *P. falciparum* K1 infected erythrocytes. In brief, cultured parasites were washed three times with serum-free RPMI medium. Pelleted infected red blood cell were lysed by mixing with a large volume (adjusted to 5% hematocrit) of 0.015% (wt/vol) saponin in 150 mM NaCl and 15 mM sodium citrate (pH 7.0) and incubated on ice for 20 min. Finally, the pelleted parasites were resuspended in 3 volumes of SSC buffer (0.15 M NaCl plus 0.015 M sodium citrate) and stored at −80° C. until further use.

50 μl of parasite lysate were solubilized in an equal volume of 2×loading buffer (1.7ml, 0.5M Tris-HCl pH 6.8, 2 ml glycerol, 4.5 ml 10% SDS, 1 ml β-mercaptoethanol, 0.8 ml bromophenol blue (0.3% w/v)) and heated to 95° C. for 10 minutes. Proteins were separated on a 10% SDS PAGE mini-gel. Separated proteins were electrophoretically transferred to a nitrocellulose filter (Protran® Nitrocellulose, BA85, Schleicher & Schuell) by semi-dry blotting. Blots were blocked with PBS containing 5% milk powder and 0.1% Tween-20 over night at 4° C. The filter was cut into strips and incubated with appropriate dilutions of immune sera or MAb in blocking buffer for 1 h at room temperature. After washing the strips three times for 10 minutes with blocking buffer, they were incubated with horseradish peroxidase conjugated goat anti-mouse IgG antibodies (Bio-Rad, Reinach, Switzerland) for two hours at room temperature. Finally, after washing as above blots were developed by addition of ECL substrate (Amersham Pharmacia Biotech, Freiburg, Germany) and exposition to Kodak Biomax light scientific imaging films according to the manufacturer's recommendations.

Example 9

This example demonstrates the generation of hybridomas and production of monoclonal antibodies (Mab). Hybridomas were generated from spleen cells of mice three days after a booster immunization with AMA49-C1 loaded IRIVs using PAI mouse myeloma cells as a fusion partner. Hybrids were selected in HAT medium and cells that secreted anti-AMA49-L1 MAbs were identified by ELISA. For large-scale MAb production, hybridoma cell lines were cultured in 1-l spinner bottles and MAbs were purified by protein G affinity chromatography. Purified MAbs were dialysed against PBS, aliquoted and stored at −80° C.

Example 10

This example shows how the Parasite culture and in vitro growth inhibition assays were performed. *P. falciparum* strain K1 was cultured as described (26). Culture medium was supplemented with 0.5% AlbuMAX (Gibco, Paisley, Scotland) as a substitute for human serum (12). Synchronization of cultures was achieved by sorbitol treatment as described (23). Serogroup A+ erythrocytes for passages were obtained from the Swiss Red Cross (Basel, Switzerland).

For in vitro growth inhibition assays, synchronous late trophozoites or schizonts were diluted with fresh red blood cells to give a parasitemia of 0.5% and were mixed with purified MAb. Final hematocrit in cultures was adjusted to 0.5%. Each culture was set up in sextuplicate in 96-well flat-bottom culture plates. After 96 h plates were centrifuged at 180 g for 5 min and culture supernatants were discarded. Pelleted erythrocytes were resuspended in 200 μl of PBS supplemented with 15 μg/ml hydroethidine fluorescent vital stain (Polysciences Inc., Warrington, Pa.) and incubated at 37° C. for 30 min. The erythrocytes were washed twice with PBS, resuspended in 400 μl PBS and analyzed in a FACScan flow cytometer (Becton-Dickinson, San Jose, Calif.) with CELLQuest 3.2.1fl software. The hydroehidine emission was detected in the FL2 channel by logarithmic amplification, and the erythrocytes were gated on the basis of their forward and sideward scatters. A total of 30000 cells per sample were analyzed. Percent inhibition was calculated from the geometric mean parasitemias of sextuplicate test and control wells as 100×(control-test)/control. Statistical significance was calculated by a two-sided t-test. Confidence intervals (CI; P<95%) were calculated by antilogging the confidence limits calculated on the log scale.

Example 11

This example shows the construction of peptide-loaded virosomes and the generation of parasite-growth reactive antibodies. A sequence comprising 45 amino acid residues from loop-I in domain III of AMA-1, $Y^{446}$KDEIKKEIE-RESKRIKLNDNDDEGNKKIIAPRIFISDDKDSLKC$^{490}$, (SEQ ID NO: 5) with a GGC sequence added to the N-terminus and an additional glycine residue at the C-terminus was synthesized by standard solid phase peptide chemistry. In order to load the peptide onto virosomes, it was conjugated through a succinate linker at the N-terminus to a regioisomer of phosphatidylethanolamine (PE) and the PE-peptide conjugate designated AMA49-L1 (FIG. 1) was incorporated into IRIV as antigen delivery system. After one pre-immunization with the influenza vaccine Inflexal, mice were immunized with AMA49-L1 loaded IRIV. All four mice immunized produced antibodies that reacted with AMA49-L1 in ELISA (FIG. 2).

The elicited antibodies were cross-reactive with blood stage parasites in IFA (FIG. 3), yielding a punctate staining pattern characteristic for AMA-1 (17, 27). Interaction of mouse anti-AMA49-L1 sera with parasite expressed AMA-1 was re-confirmed by Western blot analysis using total protein lysates of *P. falciparum* blood stage parasites (FIG. 4). The anti-AMA49-L1 antisera stained primarily proteins of an apparent molecular mass of approximately 83 and 66 kDa, which is the size of the full-length AMA-1 and of its major processed product, respectively (17, 30). Some of the anti-AMA49-L1 antisera stained an additional protein band, which may correspond to the previously described 46 kDa processing product of AMA-1 (18) that possesses the same N-terminus as the 66 kDa fragment.

Example 12

This example shows the induction of cross-reactive antibodies using the cyclized peptides of the present invention and the identification of the epitopes recognized by the antibodies. In order to investigate whether cyclization of the peptide via cysteine residues close to the C- and N-termini improves the yield of parasite binding antibodies, mice were immunized with IRIV loaded with a cyclized (AMA49-C1) and a linear (AMA49-L2) version of AMA49-L1 (FIG. 1). While AMA49-L1 contained free thiols, both thiol groups of the terminal cysteine residues were blocked by alkylation in the case of AMA49-L2. IFA titers obtained with the two constructs did not differ significantly and were comparable to those obtained with AMA49-L1(data not shown).

For a detailed analysis of the humoral immune response, AMA49-C1 specific mouse B cell hybridomas were generated. All 11 hybridoma clones obtained secreted IgG:κ (10 MAbs were IgG1, MAb DV3 was IgG2a) that reacted in ELISA both with the cyclic and the linear peptide with comparable efficacy. These 11 MAbs all stained blood stage parasites in IFA (data not shown). Competition ELISA experiments with a set of 4 overlapping linear peptides comprising the sequences $AMA^{446-462}$, $AMA^{452-472}$, $AMA^{462-482}$ and $AMA^{472-490}$ (FIG. 1) were used for epitope mapping and differentiated between four groups of antibodies (Table 2).

was blocked by the C-terminal sequence $AMA^{472-490}$. A library of 35 cyclic peptides each containing 12 residues scanning the $AMA^{444-489}$ sequence each with an offset of one amino acid, was used for more detailed epitope mapping (see FIG. 1 and Table. 2). These peptides were conformationally restrained by cyclization through linkage to a dipeptide template comprising a D-proline and an L-4-aminoproline conjugated to succPE. In ELISA, both MAbs DV2 and DV6 inhibited by $AMA^{446-462}$ bound to none of the short cyclic peptides. MAb DV7 bound to the consecutive cyclic peptides comprising residues 450–461 through 455–466, which share the sequence $E^{455}RESKR^{461}$ (SEQ ID NO:3) present also in the overlap of the two inhibitory long peptides $AMA^{446-462}$ and $AMA^{452-472}$. MAbs DV5 and DV8 bound to cyclic peptides 453–464 through 459–470, which

TABLE 2

Reactivity of anti-AMA49C1mAbs

|  | MAb: | DV2 | DV6 | DV7 | DV5 | DV8 | DV1 | DV3 | DV4 | DV9 | DV10 | DV11 |
|---|---|---|---|---|---|---|---|---|---|---|---|---|
|  | $AMA^{446-490}$ | + | + | + | + | + | + | + | + | + | + | + |
| Linear | $AMA^{446-462}$ | + | + | + | − | − | − | − | − | − | − | − |
| peptides | $AMA^{452-472}$ | − | − | + | + | + | − | − | − | − | − | − |
|  | $AMA^{462-482}$ | − | − | − | − | − | + | + | + | + | + | + |
|  | $AMA^{472-490}$ | − | − | − | − | − | − | − | − | − | − | − |
|  | $AMA^{444-455}$ | − | − | − | − | − | − | − | − | − | − | − |
|  | $AMA^{445-456}$ | − | − | − | − | − | − | − | − | − | − | − |
|  | $AMA^{446-457}$ | − | − | − | − | − | − | − | − | − | − | − |
|  | $AMA^{447-458}$ | − | − | − | − | − | − | − | − | − | − | − |
|  | $AMA^{448-459}$ | − | − | − | − | − | − | − | − | − | − | − |
|  | $AMA^{449-460}$ | − | − | − | − | − | − | − | − | − | − | − |
|  | $AMA^{450-461}$ | − | − | + | − | − | − | − | − | − | − | − |
|  | $AMA^{451-462}$ | − | − | + | − | − | − | − | − | − | − | − |
|  | $AMA^{452-463}$ | − | − | + | − | − | − | − | − | − | − | − |
|  | $AMA^{453-464}$ | − | − | + | + | + | − | − | − | − | − | − |
|  | $AMA^{454-465}$ | − | − | + | + | + | − | − | (+) | − | − | − |
|  | $AMA^{455-466}$ | − | − | + | + | + | − | − | − | − | − | − |
|  | $AMA^{456-467}$ | − | − | (+) | + | + | (+) | − | + | + | + | + |
|  | $AMA^{457-468}$ | − | − | − | + | + | (+) | − | − | − | − | − |
|  | $AMA^{458-469}$ | − | − | − | + | + | − | − | (+) | (+) | − | − |
|  | $AMA^{459-470}$ | − | − | − | + | + | − | − | − | − | − | − |
|  | $AMA^{460-471}$ | − | − | − | − | − | − | − | − | − | − | − |
|  | $AMA^{461-472}$ | − | − | − | − | − | − | − | − | − | − | − |
|  | $AMA^{462-473}$ | − | − | − | − | − | + | (+) | + | + | − | − |
|  | $AMA^{463-474}$ | − | − | − | − | − | − | − | + | + | − | − |
|  | $AMA^{464-475}$ | − | − | − | − | − | + | (+) | + | + | + | + |
|  | $AMA^{465-476}$ | − | − | − | − | − | + | (+) | + | + | + | + |
|  | $AMA^{466-477}$ | − | − | − | (+) | (+) | + | + | + | + | + | + |
|  | $AMA^{467-478}$ | − | − | − | − | − | + | (+) | + | + | + | + |
|  | $AMA^{468-479}$ | − | − | − | − | − | − | − | − | − | − | − |
|  | $AMA^{469-480}$ | − | − | − | − | − | − | − | − | − | − | − |
|  | $AMA^{470-481}$ | − | − | − | − | − | − | − | − | − | − | − |
|  | $AMA^{471-482}$ | − | − | − | − | − | − | − | − | − | − | − |
|  | $AMA^{472-483}$ | − | − | − | − | − | − | − | − | − | − | − |
|  | $AMA^{473-484}$ | − | − | − | − | − | − | − | − | − | − | − |
|  | $AMA^{474-485}$ | − | − | − | + | − | − | − | + | + | − | − |
|  | $AMA^{475-486}$ | − | − | − | − | − | − | − | − | − | − | − |
|  | $AMA^{476-487}$ | − | − | − | − | − | − | − | − | − | − | − |
|  | $AMA^{477-488}$ | − | − | − | + | + | − | − | − | − | − | − |
|  | $AMA^{478-489}$ | − | − | − | − | − | − | − | + | + | − | − |

Antigen binding of MAbs DV2 and DV6 was blocked by $AMA^{446-462}$, MAb DV7 was blocked both by $AMA^{446-462}$ and $AMA^{452-472}$, MAbs DV5 and DV8 were blocked by $AMA^{452-472}$ and MAbs DV1, DV3, DV4, DV9, DV10 and DV11 were blocked by $AMA^{462-482}$. None of the antibodies share the sequence $K^{459}RIKLN^{464}$ (SEQ ID NO: 1) located in the center of the inhibitory peptide $AMA^{452-472}$. Additional binding of both MAbs to the non-consecutive cyclic peptide 477–488 and of MAb DV5 to cyclic peptide 474–485 (PRIFISDD; (SEQ ID NO: 4)) is indicative of a discontinuous epitope. All six MAbs that were inhibited by AMA 462–482 exhibited binding to the consecutive peptides 464–475 through 467–478 which share the sequence $D^{467}DEGNKKII^{475}$ (SEQ ID NO: 2) located in the centre of the inhibitory long peptide $AMA^{462-482}$. MAb DV1 reacted in addition with the overlapping peptide 462–473. In the case of MAb DV3 the reactivity with peptide $N^{466}DDEGNKKIIAP^{477}$ (SEQ ID NO:8) was outstanding. With the other four MAbs DV4, DV9, DV10 and DV11 reactivity patterns with non-overlapping peptides indicate recognition of a discontinuous epitope. All four MAbs showed reactivity with the peptide 456–67, which only overlaps at position $D^{467}$ with the putative central $D^{467}DEGNKKII^{475}$ (SEQ ID NO: 2) recognition sequence. In addition, MAbs DV4 and DV9 also bound to the non-consecutive peptides 474–485 and 478–489 and to the peptides 462–473, 463–474 which share the sequence $D^{467}DEGNKK^{473}$ (SEQ ID NO:9) with the central recognition sequence.

Mice were immunized with IRIV loaded with PE conjugates of each of the cyclic 12-mer peptides in order to analyze whether some of them can act as mimotopes of AMA-1 surface loops and elicit parasite-binding antibodies. While all 35 structures elicited significant antibody titers against the respective immunizing peptide sequence itself, only sera raised against $AMA^{458-469}$ (containing the central recognition unit $K^{459}RIKLN^{464}$ (SEQ ID NO: 1) of MAbs DV5 and DV8) and $AMA^{464-475}$ (containing the central recognition unit $D^{467}DEGNKKII^{475}$ (SEQ ID NO: 2) of MAbs DV1, DV3, DV4, DV9, DV10 and DV11) were weakly cross-reactive with blood stage parasites in IFA (data not shown).

Example 13

This example shows the parasite growth-inhibitory effect of the antibodies elicited by use of the peptides of the invention. When Mabs DV5 and DV11 representing the two major fine specificities were tested in a *P. falciparum* in vitro growth inhibition assay, both exhibited substantial inhibitory activity (FIG. 5). A 95.3% reduction of parasite growth was observed after addition of MAb DV5 at a final concentration of 300 µg/ml (average of five independent sixtuplicated experiments). MAb DV11 also exhibited a significant, but lower growth inhibitory activity, while an isotype-matched control MAb had no effect. Taken together, these data clearly demonstrate that it is possible to elicit parasite binding and in vitro growth inhibitory antibodies by immunization with $AMA-1^{446-490}$ in combination with IRIV as a human compatible antigen delivery system.

REFERENCES

1. Amit, A. G., R. A. Mariuzza, S. E. Phillips, and R. J. Poljak. 1986. Three-dimensional structure of an antigen-antibody complex at 2.8 A resolution. Science 233:747–753.
2. Anders, R. F., P. E. Crewther, S. Edwards, M. Margetts, M. L. Matthew, B. Pollock, and D. Pye. 1998. Immunisation with recombinant AMA-1 protects mice against infection with *Plasmodium chabaudi*. Vaccine 16:240–247.
3. Barlow, D. J., M. S. Edwards, and J. M. Thornton. 1986. Continuous and discontinuous protein antigenic determinants. Nature 322:747–748.
4. Cheng, Q. and A. Saul. 1994. Sequence analysis of the apical membrane antigen I (AMA-1) of *Plasmodium vivax*. Mol. Biochem. Parasitol. 65:183–187.
5. Cohen, S., I. A. McGregor, and S. Carrington. 1961. Gamma globulin and acquired immunity to human malaria. Nature 192:733–737.
6. Coley, A. M., N. V. Campanale, J. L. Casey, A. N. Hodder, P. E. Crewther, R. F. Anders, L. M. Tilley, and M. Foley. 2001. Rapid and precise epitope mapping of monoclonal antibodies against *Plasmodium falciparum* AMA1 by combined phage display of fragments and random peptides. Protein Eng 14:691–698.
7. Collins, W. E., D. Pye, P. E. Crewther, K. L. Vandenberg, G. G. Galland, A. J. Sulzer, D. J. Kemp, S. J. Edwards, R. L. Coppel, J. S. Sullivan, C. L. Morris and R. F. Anders. 1994. Protective immunity induced in squirrel monkeys with recombinant apical membrane antigen-1 of *Plasmodium fragile*. Am. J. Trop. Med. Hyg. 51:711–719.
8. Crewther, P. E., J. G. Culvenor, A. Silva, J. A. Cooper, and R. F. Anders. 1990. *Plasmodium falciparum*: two antigens of similar size are located in different compartments of the rhoptry. Exp. Parasitol. 70:193–206.
9. Crewther, P. E., M. L. Matthew, R. H. Flegg, and R. F. Anders. 1996. Protective immune responses to apical membrane antigen 1 of *Plasmodium chabaudi* involve recognition of strain-specific epitopes. Infect. Immun. 64:3310–3317.
10. Deans, J. A., T. Alderson, A. W. Thomas, G. H. Mitchell, E. S. Lennox, and S. Cohen. 1982. Rat monoclonal antibodies which inhibit the in vitro multiplication of *Plasmodium knowlesi*. Clin. Exp. Immunol. 49:297–309.
11. Deans, J. A., A. M. Knight, W. C. Jean, A. P. Waters, S. Cohen, and G. H. Mitchell. 1988. Vaccination trials in rhesus monkeys with a minor, invariant, *Plasmodium knowlesi* 66 kD merozoite antigen. Parasite Immunol. 10:535–552.
12. Dorn, A., R. Stoffel, H. Matile, A. Bubendorf, and R. G. Ridley. 1995. Malarial haemozoin/beta-haematin supports haem polymerization in the absence of protein. Nature 374:269–271.
13. Escalante, A. A., H. M. Grebert, S. C. Chaiyaroj, M. Magris, S. Biswas, B. L. Nahlen, and A. A. Lal. 2001. Polymorphism in the gene encoding the apical membrane antigen-1 (AMA-1) of *Plasmodium falciparum*. X. Asembo Bay Cohort Project. Mol. Biochem. Parasitol. 113:279–287.
14. Gluck, R. 1999. Adjuvant activity of immunopotentiating reconstituted influenza virosomes (IRIVs). Vaccine 17:1782–1787.
15. Gomme, P. T., P. G. Stanton, and M. T. Hearn. 1999. Evaluation of a pepscan approach to identify epitopes recognised by anti-hTSH monoclonal antibodies. J. Biochem. Biophys. Methods 38:53–70.
16. Hodder, A. N., P. E. Crewther, M. L. Matthew, G. E. Reid, R. L. Moritz, R. J. Simpson, and R. F. Anders. 1996. The disulfide bond structure of Plasmodium apical membrane antigen-1. J. Biol. Chem. 271:29446–29452.
17. Hodder, A. N., P. E. Crewther, and R. F. Anders. 2001. Specificity of the protective antibody response to apical membrane antigen 1. Infect. Immun. 69:3286–3294.
18. Howell, S. A., C. Withers-Martinez, C. H. Kocken, A. W. Thomas, and M. J. Blackman. 2001. Proteolytic processing and primary structure of *Plasmodium falciparum* apical membrane antigen-1. J. Biol. Chem. 276:31311–31320.
19. Kocken, C. H., A. M. van der Wel, M. A. Dubbeld, D. L. Narum, F. M. van de Rijke, G. J. van Gemert, d. L. van, X, L. H. Bannister, C. Janse, A. P. Waters, and A. W. Thomas. 1998. Precise timing of expression of a *Plasmodium falciparum*-derived transgene in *Plasmodium* berghei is a critical determinant of subsequent subcellular localization. J. Biol. Chem. 273:15119–15124.
20. Kocken, C. H., Narumi D L, A. Massougbodji, B. Ayivi, M. A. Dubbeld, W. A. van der, D. J. Conway, A. Sanni, and A. W. Thomas. 2000. Molecular characterisation of Plasmodium reichenowi apical membrane antigen-1 (AMA-1), comparison with P. falciparum AMA-1, and antibody-mediated inhibition of red cell invasion. Mol. Biochem. Parasitol. 109:147–156.
21. Kocken, C. H., C. Withers-Martinez, M. A. Dubbeld, W. A. van der, F. Hackett, A. Valderrama, M. J. Blackman, and A. W. Thomas. 2002. High-level expression of the malaria blood-stage vaccine candidate Plasmodium falciparum apical membrane antigen 1 and induction of antibodies that inhibit erythrocyte invasion. Infect. Immun. 70:4471–4476.
22. Kumar, S., J. E. Epstein, and T. L. Richie. 2002. Vaccines against asexual stage malaria parasites. Chem. Immunol. 80:262–286.
23. Lambros, C. and J. P. Vanderberg. 1979. Synchronization of Plasmodium falciparum erythrocytic stages in culture. J. Parasitol. 65:418–420.
24. Marshall, V. M., M. G. Peterson, A. M. Lew, and D. J. Kemp. 1989. Structure of the apical membrane antigen 1 (AMA-1) of Plasmodium chabaudi. Mol. Biochem. Parasitol. 37:281–283.
25. Marshall, V. M., L. Zhang, R. F. Anders, and R. L. Coppel. 1996. Diversity of the vaccine candidate AMA-1 of Plasmodium falciparum. Mol. Biochem. Parasitol. 77:109–113.
26. Matile, H. and J. Pink. 1990. Plasmodium falciparum malaria parasite cultures and their use in immunology, p.221–234. In I. Lefkovits and P. Benvenuto (ed.), Immunological methods. Academic Press, Inc., San Diego, Calif.
27. Miller, L. H. and S. L. Hoffman. 1998. Research toward vaccines against malaria. Nat. Med. 4:520–524.
28. Moreno, R., L. Jiang, K. Moehle, R. Zurbriggen, R. Gluck, J. A. Robinson, and G. Pluschke. 2001. Exploiting conformationally constrained peptidomimetics and an efficient human-compatible delivery system in synthetic vaccine design. Chembiochem 2:838–843.
29. Nair, M., M. Hinds, A. Coley, A. Hodder, M. Foley, R. Anders, and R. Norton. 2002. Structure of Domain III of the Blood-stage Malaria Vaccine Candidate, Plasmodium falciparum Apical Membrane Antigen 1 (AMA1). J. Mol. Biol. 322:741–753.
30. Narum, D. L. and A. W. Thomas. 1994. Differential localization of full-length and processed forms of PF83/AMA-1 an apical membrane antigen of Plasmodium falciparum merozoites. Mol. Biochem. Parasitol. 67:59–68.
31. Narum, D. L., S. A. Ogun, A. W. Thomas, and A. A. Holder. 2000. Immunization with parasite-derived apical membrane antigen 1 or passive immunization with a specific monoclonal antibody protects BALB/c mice against lethal Plasmodium yoelii yoelii YM blood-stage infection. Infect. Immun. 68:2899–2906.
32. Peterson, M. G., V. M. Marshall, J. A. Smythe, P. E. Crewther, A. Lew, A. Silva, R. F. Anders, and D. J. Kemp. 1989. Integral membrane protein located in the apical complex of Plasmodium falciparum. Mol. Cell Biol. 9:3151–3154.
33. Polley, S. D. and D. J. Conway. 2001. Strong diversifying selection on domains of the Plasmodium falciparum apical membrane antigen 1 gene. Genetics 158:1505–1512.
34. Poltl-Frank, F., R. Zurbriggen, A. Heig, F. Stuart, J. Robinson, R. Gluck, and G. Pluschke. 1999. Use of reconstituted influenza virus virosomes as an immunopotentiating delivery system for a peptide-based vaccine. Clin. Exp. Immunol. 117:496–503.
35. Richie, T. L. and A. Saul. 2002. Progress and challenges for malaria vaccines. Nature 415:694–701.
36. Sabchareon, A., T. Burnouf, D. Ouattara, P. Attanath, H. Bouharoun-Tayoun, P. Chantavanich, C. Foucault, T. Chongsuphajaisiddhi, and P. Druilhe. 1991. Parasitologic and clinical human response to immunoglobulin administration in falciparum malaria. Am. J. Trop. Med. Hyg. 45:297–308.
37. Salvatore, D., A. Hodder, W. Zeng, L. Brown, R. Anders, and D. Jackson. 2002. Identification of antigenically active tryptic fragments of apical membrane antigen-1 (AMA1) of Plasmodium chabaudi malaria: strategies for assembly of immunologically active peptides. Vaccine 20:3477–3484.
38. Sheriff, S., E. W. Silverton, E. A. Padlan, G. H. Cohen, S. J. Smith-Gill, B. C. Finzel, and D. R. Davies. 1987. Three-dimensional structure of an antibody-antigen complex. Proc. Natl. Acad. Sci. U. S. A 84:8075–8079.
39. Triglia, T., J. Healer, S. R. Caruana, A. N. Hodder, R. F. Anders, B. S. Crabb, and A. F. Cowman. 2000. Apical membrane antigen 1 plays a central role in erythrocyte invasion by Plasmodium species. Mol. Microbiol. 38:706–718.
40. Urquiza, M., J. E. Suarez, C. Cardenas, R. Lopez, A. Puentes, F. Chavez, J. C. Calvo, and M. E. Patarroyo. 2000. Plasmodium falciparum AMA-1 erythrocyte binding peptides implicate AMA-1 as erythrocyte binding protein. Vaccine 19:508–513.
41. Uthaipibull, C., B. Aufiero, S. E. Syed, B. Hansen, J. A. Guevara Patino, E. Angov, I. T. Ling, K. Fegeding, W. D. Morgan, C. Ockenhouse, B. Birdsall, J. Feeney, J. A. Lyon, and A. A. Holder. 2001. Inhibitory and blocking monoclonal antibody epitopes on merozoite surface protein 1 of the malaria parasite Plasmodium falciparum. J. Mol. Biol. 307:1381–1394.
42. Verra, F. and A. L. Hughes. 2000. Evidence for ancient balanced polymorphism at the Apical Membrane Antigen-1 (AMA-1) locus of Plasmodium falciparum. Mol. Biochem. Parasitol. 105:149–153.
43. Waters, A. P., A. W. Thomas, J. A. Deans, G. H. Mitchell, D. E. Hudson, L. H. Miller, T. F. McCutchan, and S. Cohen. 1990. A merozoite receptor protein from Plasmodium knowlesi is highly conserved and distributed throughout Plasmodium. J. Biol. Chem. 265:17974–17979.
44. WHO. 1997. World malaria situation in 1994. Weekly Epidemiol. Rec. 69:309–314.
45. Xu, H., A. N. Hodder, H. Yan, P. E. Crewther, R. F. Anders, and M. F. Good. 2000. CD4+ T cells acting independently of antibody contribute to protective immunity to Plasmodium chabaudi infection after apical membrane antigen 1 immunization. J. Immunol. 165:389–396.
46. Zhang, L., B. Zhan, J. Wang, and X. Feng. 1995. Sequence analysis of apical membrane antigen 1 from a Plasmodium falciparum isolate collected from Mengpeng Township, Yunnan Province. Zhongguo Ji. Sheng Chong. Xue. Yu Ji. Sheng Chong. Bing. Za Zhi. 13:203–208.

We claim:

1. An immunostimulatory composition consisting of the polypeptide of SEQ ID NO: 5 or functional variants thereof.

2. The composition of claim 1 wherein the polypeptide is cyclized.

3. The composition of claim 2, wherein the polypeptide is cyclized by intramolecular crosslink.

4. The composition of claim 2, wherein the polypeptide is cyclized by template.

5. The composition of claim 2, wherein the polypeptide further comprises C -and N-terminal spacer and crosslinking residues.

6. The composition of claim 5, wherein the crosslinking residues are selected from the group consisting of cysteine, bromoacetyl and maleimidyl residues.

7. The composition of claim 5, wherein the spacer residues are selected from the group consisting of glycine, alanine, seine, asparagine and glutamine residues.

8. An immunostimulatory composition consisting of the polypeptide of SEQ ID NO: 6 or functional variants thereof.

9. The composition of claim 8, wherein the polypeptide is cyclized.

10. The composition of claim 9, wherein the polypeptide is cyclized by intramolecular crosslink.

11. The composition of claim 10, wherein said crosslink is between N- and C -terminally located cysteine residues.

12. An immunostimulatory composition consisting of the polypeptide of SEQ ID NO: 7 or functional variants thereof.

13. The composition of claim 12, wherein the polypeptide is cyclized by intramolecular crosslink.

14. The composition of claim 13, wherein said crosslink is between N- and C-terminally located cysteine residues.

15. The composition of claims 1–14 further comprising an adjuvant.

16. The composition of claim 15 further comprising a delivery vehicle.

17. The composition of claim 16, wherein said delivery vehicle is selected from the group consisting of virosomes and liposomes.

18. The composition of claim 16, wherein the immunostimulatory composition is attached to the surface of said delivery vehicle.

19. The composition of claim 16, wherein said immunostimulatory composition is encapsulated by said delivery vehicle.

20. A method of eliciting a malaria parasite growth inhibitory immune response in a host, comprising introducing into the host the composition of claim 15.

21. A method of generating antibodies against AMA-1, comprising introducing into a host the composition of claim 15.

22. A kit comprising the composition of claim 15.

23. The composition of claim 15, wherein said functional variants comprise an amino acid change selected from the group consisting of D448 to N448, K451 to M451, K485 to I485, K473 to E473, and deletion of D484.

24. The composition of claim 12, wherein the polypeptide is cyclized.

* * * * *

SEQUENCE LISTING

<160> NUMBER OF SEQ ID NOS: 7

<210> SEQ ID NO 1
<211> LENGTH: 6
<212> TYPE: PRT
<213> ORGANISM: P.falciparum

<400> SEQUENCE: 1

Lys Arg Ile Lys Leu Asn
1               5

<210> SEQ ID NO 2
<211> LENGTH: 9
<212> TYPE: PRT
<213> ORGANISM: P.falciparum

<400> SEQUENCE: 2

Asp Asp Glu Gly Asn Lys Lys Ile Ile
1               5

<210> SEQ ID NO 3
<211> LENGTH: 7
<212> TYPE: PRT
<213> ORGANISM: P.falciparum

<400> SEQUENCE: 3

Glu Arg Glu Ser Lys Arg Ile
1               5

<210> SEQ ID NO 4
<211> LENGTH: 8
<212> TYPE: PRT
<213> ORGANISM: P.falciparum

<400> SEQUENCE: 4

Pro Arg Ile Phe Ile Ser Asp Asp
1               5

<210> SEQ ID NO 5
<211> LENGTH: 45
<212> TYPE: PRT
<213> ORGANISM: P.falciparum

<400> SEQUENCE: 5

Tyr Lys Asp Glu Ile Lys Lys Glu Ile Glu Arg Glu Ser Lys Arg Ile
1               5                   10                  15
Lys Leu Asn Asp Asn Asp Asp Glu Gly Asn Lys Lys Ile Ile Ala Pro
            20                  25                  30
Arg Ile Phe Ile Ser Asp Asp Lys Asp Ser Leu Lys Cys
        35                  40                  45

<210> SEQ ID NO 6
<211> LENGTH: 46
<212> TYPE: PRT
<213> ORGANISM: P.falciparum

<400> SEQUENCE: 6

Cys Tyr Lys Asp Glu Ile Lys Lys Glu Ile Glu Arg Glu Ser Lys Arg
1               5                   10                  15
Ile Lys Leu Asn Asp Asn Asp Asp Glu Gly Asn Lys Lys Ile Ile Ala
            20                  25                  30

```
Pro Arg Ile Phe Ile Ser Asp Asp Lys Asp Ser Leu Lys Cys
        35                  40                  45

<210> SEQ ID NO 7
<211> LENGTH: 49
<212> TYPE: PRT
<213> ORGANISM: P.falciparum

<400> SEQUENCE: 7

Gly Gly Cys Tyr Lys Asp Glu Ile Lys Lys Glu Ile Glu Arg Glu Ser
1               5                   10                  15

Lys Arg Ile Lys Leu Asn Asp Asn Asp Asp Glu Gly Asn Lys Lys Ile
            20                  25                  30

Ile Ala Pro Arg Ile Phe Ile Ser Asp Asp Lys Asp Ser Leu Lys Cys
        35                  40                  45

Gly
```